United States Patent
Kong et al.

(10) Patent No.: US 10,570,445 B2
(45) Date of Patent: *Feb. 25, 2020

(54) FRET-LABELED COMPOUNDS AND USES THEREFOR

(71) Applicant: Pacific Biosciences of California, Inc., Menlo Park, CA (US)

(72) Inventors: Xiangxu Kong, Union City, CA (US); Gene Shen, Santa Clara, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,541

(22) Filed: Jul. 30, 2018

(65) Prior Publication Data

US 2019/0032117 A1    Jan. 31, 2019

Related U.S. Application Data

(63) Continuation of application No. 15/379,118, filed on Dec. 14, 2016, now Pat. No. 10,066,258, which is a
(Continued)

(51) Int. Cl.
*C12Q 1/68* (2018.01)
*C12Q 1/6869* (2018.01)
(Continued)

(52) U.S. Cl.
CPC ......... *C12Q 1/6869* (2013.01); *C07H 19/207* (2013.01); *C12Q 1/6818* (2013.01);
(Continued)

(58) Field of Classification Search
CPC .................................................. C12Q 1/6869
(Continued)

(56) References Cited

U.S. PATENT DOCUMENTS

| 4,981,977 A | 1/1991 | Southwick et al. |
| 5,328,824 A | 7/1994 | Ward et al. |

(Continued)

FOREIGN PATENT DOCUMENTS

| EP | 1105529 B1 | 11/2005 |
| JP | H05-60698 | 3/1998 |

(Continued)

OTHER PUBLICATIONS

Beckett et al., "A minimal peptide substrate in biotin holoenzyme synthetase-catalyzed biotinylation," Protein Sci (1999) 8:921-929.
(Continued)

*Primary Examiner* — Jezia Riley
(74) *Attorney, Agent, or Firm* — David C. Scherer

(57) ABSTRACT

FRET-labeled compounds are provided for use in analytical reactions. In certain embodiments, FRET-labeled nucleotide analogs are used in place of naturally occurring nucleoside triphosphates or other analogs in analytical reactions comprising nucleic acids, for example, template-directed nucleic acid synthesis, DNA sequencing, RNA sequencing, single-base identification, hybridization, binding assays, and other analytical reactions.

14 Claims, 14 Drawing Sheets

Related U.S. Application Data continuation of application No. 13/427,611, filed on Mar. 22, 2012, now Pat. No. 9,551,660, which is a continuation of application No. 12/749,859, filed on Mar. 30, 2010, now Pat. No. 8,927,212.

(60) Provisional application No. 61/164,567, filed on Mar. 30, 2009.

(51) Int. Cl.
| | |
|---|---|
| C07H 19/207 | (2006.01) |
| G01N 33/542 | (2006.01) |
| G01N 33/58 | (2006.01) |
| G01N 21/64 | (2006.01) |
| C12Q 1/6818 | (2018.01) |

(52) U.S. Cl.
CPC ....... *G01N 21/6428* (2013.01); *G01N 33/542* (2013.01); *G01N 33/582* (2013.01); *G01N 2021/6441* (2013.01); *Y10T 436/143333* (2015.01)

(58) Field of Classification Search
USPC .......................................................... 435/6.1
See application file for complete search history.

(56) References Cited

U.S. PATENT DOCUMENTS

| | | | |
|---|---|---|---|
| 5,476,928 A | 12/1995 | Ward et al. | |
| 5,654,419 A | 8/1997 | Mathies et al. | |
| 5,688,648 A | 11/1997 | Mathies et al. | |
| 5,723,584 A | 3/1998 | Schatz | |
| 5,853,992 A | 12/1998 | Glazer et al. | |
| 5,863,727 A | 1/1999 | Lee et al. | |
| 5,874,239 A | 2/1999 | Schatz | |
| 5,932,433 A | 8/1999 | Schatz | |
| 5,945,526 A | 8/1999 | Lee et al. | |
| 6,008,373 A | 12/1999 | Waggoner et al. | |
| 6,150,107 A | 11/2000 | Glazer et al. | |
| 6,177,249 B1 | 1/2001 | Kwok et al. | |
| 6,255,083 B1 | 7/2001 | Williams | |
| 6,335,440 B1 | 1/2002 | Lee et al. | |
| 6,348,596 B1 | 2/2002 | Lee et al. | |
| 6,479,303 B1 | 11/2002 | Waggoner et al. | |
| 6,545,164 B1 | 4/2003 | Waggoner et al. | |
| 6,696,255 B2 | 2/2004 | Dattagupta | |
| 6,849,745 B2 | 2/2005 | Lee et al. | |
| 6,908,769 B2 | 6/2005 | Belik et al. | |
| 6,917,726 B2 | 7/2005 | Levene et al. | |
| 6,972,198 B2 | 12/2005 | Craig et al. | |
| 7,013,054 B2 | 3/2006 | Levene et al. | |
| 7,015,000 B2 | 3/2006 | Mathies et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,170,050 B2 | 1/2007 | Turner et al. | |
| 7,181,122 B1 | 2/2007 | Levene et al. | |
| 7,292,742 B2 | 11/2007 | Levene et al. | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,405,281 B2 | 7/2008 | Xu et al. | |
| 7,476,503 B2 | 1/2009 | Turner et al. | |
| 7,805,081 B2 | 9/2010 | Lundquist et al. | |
| 8,927,212 B2 | 1/2015 | Kong et al. | |
| 9,551,660 B2 | 1/2017 | Kong et al. | |
| 10,066,258 B2 * | 9/2018 | Kong .................. | C07H 19/207 |
| 2002/0168641 A1 | 11/2002 | Mortensen et al. | |
| 2003/0044781 A1 | 3/2003 | Korlach et al. | |
| 2003/0124576 A1 | 7/2003 | Kumar et al. | |
| 2003/0143594 A1 | 7/2003 | Mathies et al. | |
| 2004/0076979 A1 | 4/2004 | Belik et al. | |
| 2004/0086889 A1 | 5/2004 | Hwang et al. | |
| 2004/0241716 A1 | 12/2004 | Kumar et al. | |
| 2007/0036511 A1 | 2/2007 | Lundquist et al. | |
| 2007/0095119 A1 | 5/2007 | Varadachari | |
| 2007/0128133 A1 | 6/2007 | Eid et al. | |
| 2007/0161017 A1 | 7/2007 | Eid et al. | |
| 2007/0219367 A1 | 9/2007 | Shchepinov et al. | |
| 2008/0128627 A1 | 6/2008 | Lundquist et al. | |
| 2008/0152280 A1 | 6/2008 | Lundquist et al. | |
| 2008/0152281 A1 | 6/2008 | Lundquist et al. | |
| 2008/0176241 A1 | 7/2008 | Eid et al. | |
| 2008/0226307 A1 | 9/2008 | Lundquist et al. | |
| 2008/0241866 A1 | 10/2008 | Korlach et al. | |
| 2008/0277595 A1 | 11/2008 | Zhong et al. | |
| 2008/0299565 A1 | 11/2008 | Schneider et al. | |
| 2009/0024331 A1 | 1/2009 | Tomaney et al. | |
| 2009/0094763 A1 | 4/2009 | Dawis et al. | |
| 2009/0208957 A1 | 8/2009 | Korlach et al. | |
| 2009/0233302 A1 | 9/2009 | Wegener et al. | |
| 2010/0009872 A1 | 1/2010 | Gray et al. | |
| 2010/0065726 A1 | 3/2010 | Zhong et al. | |
| 2010/0136592 A1 | 6/2010 | Lee et al. | |
| 2010/0221716 A1 | 9/2010 | Flusberg et al. | |
| 2017/0292157 A1 | 10/2017 | Drmanac | |

FOREIGN PATENT DOCUMENTS

| | | |
|---|---|---|
| WO | 2007041394 A2 | 4/2007 |
| WO | 2007075873 A2 | 7/2007 |
| WO | 2007075987 A2 | 7/2007 |
| WO | 2007076057 A2 | 7/2007 |
| WO | 2009056831 A1 | 5/2009 |

OTHER PUBLICATIONS

Beier et al., "Versatile Derivatisation of Solid Support Media for Covalent Bonding on DNA-Microchips," Nucl. Acids Res. (1999) 27:1970-1977.

Deval et al., "Mechanistic Insights into the Suppression of Drug Resistance by Human Immunodeficiency Virus Type 1 Reverse Transcriptase Using—Boranophosphate Nucleoside Analogs," J. Biol. Chem. (2005) 280:3838-3846.

Eid, et al., "Real-Time DNA Sequencing from Polymerase Molecules," Science (2009) 323:133-138.

Ernst et al., "Cyanine dye labeling reagents for sulfhydryl groups," Cytometry (1989) 10:3-10.

Hung et al., "Cyanine Dyes with High Absorption Cross Section as Donor Chromophores in Energy Transfer Primers.sup.1." Anal. Biochem (1996) 243(1):15-27.

Korlach et al., "Selective aluminum passivation for targeted immobilization of single DNA polymerase molecules in zero-mode waveguide nanostructures" PNAS (2008) 105:1176-1181.

Levene et al., "Zero-mode waveguides for single moledule analysis at high concentrations" Science (2003) 299:682-686.

Mujumdar, et al., "Cyanine Dye Labeling Reagents Containing Isothiocyanate Groups.sup.1" Cytometry *(1989) 10:11-19.

Mujumbar, et al., "Cyanine Dye Labeling Reagents: Sulfoindocyanine Succinimidyl Esters" Bioconjugate Chemistry (1993) 4(2):105-111.

Meyer, P. et al., "Structural basis for activation of—boranophosphate nucleotide analogues targeting drug-resistant reverse transcriptase," EMBO J. (2000) 19:3520-3529.

Ramsey-Shaw et al. "Reading, Writing and Modulating Genetic Information with Boranophosphate Mimics of Nucleotides, DNA, and RNA" Ann NY Acad. Sci. (2003) 1002:12-29.

Schuler, B. et al., "Polyproline and the 'spectroscopic ruler' revisited with single-molecule fluorescence" PNAS (2005) 102(8):2754-2759.

Southwick et al., "Cyanine Dye Labeling Reagents—Carboxymethylindocyanine Succinimidyl Esters," Cytometry (1990) 11:418-430.

International Search Report and Written Opinion dated Jan. 24, 2011 for related case PCT/US2010/000948.

(56) References Cited

OTHER PUBLICATIONS

Koushik et al., "Cerulean, Venus and VenusY67C FRET Reference Standards," Biophysical Journ: Biophysical Lett (2006) 91(12):L99-L101.

* cited by examiner

Linear Linkers:

Tridentate Linkers:

FRET-LABELED COMPOUNDS AND USES THEREFOR

CROSS-REFERENCE TO RELATED APPLICATIONS

This application is a continuation of U.S. patent application Ser. No. 15/379,118 filed Dec. 14, 2016, which is a continuation of U.S. patent application Ser. No. 13/427,611 filed Mar. 22, 2012, which is a continuation of U.S. patent application Ser. No. 12/749,859 filed Mar. 30, 2010, which claims the benefit of U.S. Provisional Application No. 61/164,567, filed Mar. 30, 2009, the disclosure of which are incorporated herein by reference in their entirety for all purposes.

STATEMENT REGARDING FEDERALLY SPONSORED RESEARCH

Not Applicable.

BACKGROUND OF THE INVENTION

In the analysis of biological processes, researchers are constantly looking for new and better ways to monitor and analyze both the individual reactions that make up complex biological systems, as well as observe the operation of those systems as a whole. In doing so, researchers have developed methods, systems, and compositions that employ artificially labeled molecules as model constituents for those reactions and systems. Observation of the model molecules is facilitated by the presence of the labeling group. Such labels include radioactive compounds or radiolabels, chromophores that absorb and/or emit light of different wavelengths to provide colored indications of an event, chemiluminescent labels that can spontaneously emit light in response to a particular chemical event, fluorescent labels that emit light in response to excitation by light of a different wavelength, and reporter system labels that provide an exogenous, assayable activity or property to indicate the presence, absence or change in the model molecule. Such reporter labels often include exogenous enzymes, binding molecules or the like that are capable of being identified and even quantified.

In attaching label groups to different model reaction constituents, one runs the risk that the presence of the label will adversely impact the reaction being observed. For example, large hydrophobic labeling groups can present issue of steric interference with the progress of the reaction of interest by blocking or not properly interacting with the other reaction constituents. Likewise, labeling components that impact the chemical properties of the model compound or the reaction environment can similarly adversely impact reaction conditions. In other cases, the properties of the label itself may adversely affect the reaction components. For example, the presence of fluorescent molecules in close proximity to enzymatic reaction components can lead to decay in the level of enzyme activity through photo-chemically induced reaction intermediates or other impacts.

Further, certain such analyses require the use of multiple labels to monitor multiple different reaction constituents and/or products. For example, in certain sequencing-by-synthesis applications each type of nucleotide (e.g., A, G, T, and C) is tagged with a different label, and a synthesis reaction is carried out to construct a nascent nucleic acid strand using a sample nucleic acid as a template. At each position on the template strand, a nucleotide complementary to the template strand is incorporated into the nascent strand. The newly incorporated nucleotide can be identified by various means, including detection of a signal from a label it carries. The sequence of the template strand is derived from the sequence of complementary nucleotides detected upon incorporation into the nascent strand. Detection of multiple different labels in a single analytical reaction adds significant complexity to data analysis, and variability in the performance of the multiple labels can also adversely affect the ability to "read" the template nucleic acid by virtue of synthesis of the complementary nascent strand.

Accordingly, it would be desirable to provide reaction components that provide remedies to some of the issues created by the incorporation of labeling groups onto components of analytical reactions. The present invention provides these and other solutions.

SUMMARY OF THE INVENTION

In certain aspects, the present invention is generally directed to compounds comprising detectable labels that undergo Förster resonance energy transfer (FRET), and these labeled compounds are particularly useful in certain analytical reactions. Such detectable labels are termed "FRET labels" herein, and typically comprise at least two chromophores that engage in FRET such that at least a portion of the energy absorbed by at least one "donor chromophore" is transferred to at least one "acceptor chromophore," which emits at least a portion of the transferred energy as a detectable signal contributing to an emission spectrum. In certain preferred embodiments, at least two chromophores in a FRET label emit detectable signals that contribute to a resulting emission spectrum comprising at least two peaks. Such a FRET label can be termed a "multi-spectral" construct (or a "dual-spectral" construct when the emission spectrum has only two peaks). In certain aspects, the chromophores are configured on the compound in order to achieve a desired efficiency of the energy transfer between the donor and acceptor chromophore, where the desired efficiency is chosen to ensure a desired emission intensity (or range thereof) at one or more emission wavelengths. In certain preferred embodiments, more than one such labeled compound is present in a single analytical reaction, wherein each labeled compound has an emission spectrum that is distinguishable from the emission spectrum of every other labeled compound in the analytical reaction such that the identity of each compound can be unambiguously determined. In preferred embodiments, the emission spectra of certain multiple labeled compounds in an analytical reaction are distinguishable from one another due to variations in emission intensity at one or more wavelengths as a result of variations in FRET efficiency. In certain embodiments, the multiple different labeled compounds comprise the same set of chromophores, but have a different configuration and therefore different emission spectra based at least in part on different FRET efficiencies. In some embodiments, non-FRET-labeled compounds also present in the analytical reactions have emission spectra that are distinct from the emission spectra of the FRET-labeled compounds of the invention.

In some aspects, the labeled compounds of the invention are analogous to nucleotides and in preferred aspects are readily processed by nucleic acid processing enzymes, such as polymerases. In certain aspects, such labeled compounds have incorporation efficiencies that are better than or at least comparable to triphosphate, tetraphosphate, pentaphosphate, or hexaphosphate analogs.

In certain embodiments, a compound is provided in an analytical reaction that comprises a label portion comprising a FRET label and a reactant portion, and wherein the FRET label has an emission spectrum comprising at least two peaks that distinctly identify the reactant portion in the analytical reaction. In certain preferred embodiments, the FRET label comprises at least two fluorophores. The compound may also include a linker portion that maintains a particular orientation of the FRET label that ensures a desired FRET efficiency. In certain embodiments, the reactant portion comprises a nucleotide or nucleotide analog, a tRNA analog, a substrate for an enzyme (e.g., a polymerase), a ligand for a receptor, or an antigen. In some embodiments, a labeled compound is provided comprising a reactant portion capable of reacting with a first enzyme, a label portion comprising a FRET label, and a linker portion coupling the label portion to the reactant portion, wherein the linker portion maintains a desired conformation of the FRET label, wherein the desired conformation results in inefficient energy transfer between chromophores in the FRET label to produce a distinct and identifiable emission spectrum.

In some embodiments, compositions of the invention include a plurality of FRET-labeled compounds having optically distinct emission spectra, even in embodiments in which they comprise the same set of chromophores. For example, although two FRET-labeled compounds contain the same two or more chromophores and emit at the same wavelengths, they are configured such that the emission intensities at those wavelengths are different and can be used to optically distinguish between the two compounds. In preferred embodiments, such optical distinction is due at least in part to differing FRET efficiencies in the two FRET-labeled compounds, which typically differ by at least about 5%, 10%, 15%, 20%, 25%, 30%, 40%, 50%, 60%, 70%, 80%, or 90%. For example, if one FRET-labeled compound has a FRET efficiency of 10% and a second FRET-labeled compound has a FRET efficiency of 90%, they differ by 80% FRET efficiency. FRET-labeled compounds in a single analytical reaction can have FRET labels comprising some or all of the same chromophores, e.g., fluorophores. Some analytical reactions comprising FRET-labeled compounds also comprise labeled compounds that are non-FRET labeled, and such non-FRET-labeled compounds can comprise a chromophore (e.g., fluorophore) present in one of the FRET-labeled compounds. For example, compositions of the invention can include nucleotides and/or nucleotide analogs coupled to a label portion that does not comprise a FRET label. Compositions of the invention can further include one or more enzymes (e.g., polymerases), receptors, antibodies, molecular complexes (e.g., ribosomes), or nucleic acids (e.g., RNA, DNA, primers, templates, etc.). Further, methods of the invention can comprise monitoring an analytical reaction. For example, monitoring of a nucleic acid synthesis reaction can comprise contacting a polymerase/template/primer complex with such a FRET-labeled compound and detecting a characteristic signal from the label portion indicative of incorporation of the nucleotide or nucleotide analog into a primer extension reaction, preferably in real time, e.g., during the incorporation.

Further, methods are provided for making various compounds comprising a FRET label that include determining a desired FRET efficiency (e.g., less than 100% of a maximal FRET efficiency for a given combination of labels), computing a conformation to achieve the desired FRET efficiency, and synthesizing the conformation. For example, a desired FRET efficiency can be 0%, 5%, 10%, 15%, 20%, 25%, 30%, 35%, 40%, 45%, 50%, 55%, 60%, 65%, 70%, 75%, 80%, 85%, 90%, or 95 of the maximum FRET efficiency. Also provided are methods for designing a plurality of FRET labels, e.g., for use in differentially labeling a plurality of compounds in a single analytical reaction. Such methods generally comprise selecting at least two chromophores for inclusion in the plurality of FRET labels, wherein each can serve as a donor or acceptor for another, and further determining a set of FRET efficiency values, such that the FRET efficiency value for each of the FRET labels is different from the FRET efficiency value for every other. A distance between the chromophores that will achieve each FRET efficiency value is computed to generate a set of distances for the plurality of FRET labels. Finally, a set of linkers is generated that comprises one linker for each of the distances in the set, wherein each linker is configured to separate the chromophores in a single of the plurality of FRET labels by a single distance in the set of distances. In preferred embodiments, each of the plurality of FRET labels generates a set of emission intensities at a set of emission wavelengths in an emission spectrum that is different from that of every other FRET label, e.g., varying the FRET efficiencies by at least about 5%, 10%, 15%, 20%, 25%, 30%, 40%, 50%, 60%, 70%, 80%, or 90%.

In certain embodiments, a composition is provided comprising a first compound and a second compound, both of which comprise a reactant portion and FRET label, wherein the emission spectrum from the first compound is distinct from the emission spectrum of the second compound. In some preferred embodiments, the emission spectra from the first compound and the second compound both comprise peaks at the same wavelengths, e.g., a first and second wavelength, but wherein the emission intensities at those wavelengths are different between the two compounds. In some preferred embodiments, a composition of the invention comprises a first compound with a first FRET label having a first FRET efficiency and a second compound with a second FRET label having a second FRET efficiency that is different from the first FRET efficiency, e.g. differing by at least about 5%,10%, 15%, 20%, 25%, 30%, 40%, 50%, 60%, 70%, 80%, or 90%. In some embodiments, the two FRET labels share at least one or more chromophores. In some embodiments, the composition further comprises at least one compound, (e.g., nucleotide or nucleotide analog) labeled with a single chromophore (e.g., fluorophore), that may also be present in at least one FRET label in the composition. In some embodiments, the composition further comprises an enzyme, a nucleic acid template, and/or a primer.

The present invention also provides methods for using the compounds described herein in performing analytical reactions, such as nucleic acid analyses, and particularly nucleic acid sequence analyses. In certain embodiments, the analytical reactions of the invention comprise providing a template nucleic acid complexed with a polymerase enzyme in a template-dependent polymerization reaction to produce a nascent nucleic acid strand, contacting the polymerase and template nucleic acid with a FRET-labeled compound of the invention, detecting whether or not the FRET-labeled compound was incorporated into the nascent strand during the polymerization reaction, and identifying a base in the template strand based upon incorporation of the FRET-labeled compound. In some such reactions, at least one or two of the nucleotide analogs is a FRET-labeled compound and at least one or two of the nucleotide analogs does not comprise a FRET label, and identification of the incorporated nucleotide analog is based at least in part on a comparison of the emission spectra generated during polymerization of the nascent strand. In preferred embodiments, incorporation of labeled nucleotide analogs, whether FRET-labeled or non-FRET-labeled, is detected in real-time during nascent strand synthesis. Preferably, the foregoing process is carried out so as to permit observation of individual nucleotide incorporation reactions, through the use of, for example, an optical confinement, that allows observation of an individual polymerase enzyme, or through the use of a heterogeneous assay system, where label groups released from incorporated analogs are detected.

In certain embodiments, methods are provided for distinguishing between two labeled compounds in an analytical reaction, e.g., by labeling the first labeled compound with a FRET pair in a first orientation ensuring a first FRET efficiency, labeling the second labeled compound with the FRET pair in a second orientation ensuring a second FRET efficiency, combining the two labeled compounds in an analytical reaction, subjecting the analytical reaction to excitation radiation, detecting a signal emitted from the analytical reaction, and analyzing the signal to determine a signal FRET efficiency. If the signal FRET efficiency is equal to the first FRET efficiency the signal originated from the first labeled compound, and if the signal FRET efficiency is equal to the second FRET efficiency the signal originated from the second labeled compound, and the two labeled compounds are thereby distinguished in the analytical reaction. Analyzing the signals emitted from an analytical reaction typically involves determining emission intensities at emission wavelengths in emission spectra. In certain preferred embodiments, a single radiation wavelength of the excitation radiation excites both the FRET pair in the first orientation and the FRET pair in the second orientation. In some embodiments, four labeled compounds are distinguished from one another by also including in the analytical reaction a third labeled compound with the first chromophore of the FRET pair (but not the second chromophore) and a fourth labeled compound with the second chromophore of the FRET pair (but not the first). If the signal FRET efficiency is not equal to either the first FRET efficiency nor the second FRET efficiency, the signal is further analyzed to determine if it is characteristic of an emission spectrum of the first chromophore or the second chromophore, thereby identifying the origin of the signal as being the third labeled compound or the fourth labeled compound, respectively. As such, four different labeled compounds are distinguishable from one another in an analytical reaction using only two chromophores, e.g., by labeling two of the compounds with a single different chromophore, and by labeling the other two compounds with FRET labels containing both chromophores in different conformations to provide detectably different emission spectra.

Further, methods are provided for identification and detection of individual labeled reactants in a reaction mixture comprising multiple different reactants, where the reactants can be nucleic acids (e.g., nucleotides or nucleotide analogs, nucleic acid segments, primers, etc.), tRNA analogs, ligands for a receptor, antigens, binding partners, etc. For example, each of the multiple different reactants are labeled with detectably different chromophore-containing labels, at least two of which are FRET labels that emit at substantially similar wavelengths but a distinctly different emission intensities. The different reactants are combined in a reaction mixture, and individual labeled reactants are detected by exposing the reaction mixture to excitation radiation and detecting an emission spectrum of each of said chromophore-containing labels. In certain preferred embodiments, a single radiation wavelength of the excitation radiation excites the FRET pairs in the reaction mixture. In certain preferred embodiments, a first of the FRET labels in the reaction mixture is configured to ensure a first distance between the constituent chromophores and a second of the FRET labels in the reaction mixture is configured to ensure a distance between the constituent chromophores that is different than the first distance. In some embodiments, the two distances are chosen to ensure inefficient energy transfer resulting in submaximal FRET efficiencies, thereby producing distinct and multi-peak (e.g., multi-spectral or dual-spectral) emission spectra. For example, the multi-peak emission spectra typically comprise a peaks resulting from emission from both the donor and acceptor chromophore in a FRET label. The different FRET labels in such reaction mixtures typically comprise different linkers that are structurally different from one another, e.g., that provide for a different spacing or distance between their constituent chromophores. In some embodiments, at least one of the chromophore-containing labels is not a FRET label, and such non-FRET labels may comprise a chromophore that is identical to a chromophore in at least one FRET label in the reaction mixture. In some preferred embodiments, the labeled reactants are nucleotide analogs comprising a single nucleobase.

In further embodiments, methods are provided for determining an identity and relative position of a nucleotide in a template nucleic acid sequence. For example, a template nucleic acid is provided and complexed with a polymerase enzyme capable of template-dependent synthesis of a complementary nascent nucleic acid strand. This complex is contacted with a plurality of differentially labeled compounds, each of which comprises an individually detectable label, wherein a subset (e.g., 1-3) of the plurality of differentially labeled compounds comprises an individually detectable label that undergoes resonance energy transfer (e.g., at a submaximal efficiency, e.g., less than 90%), and a subset (e.g., 1-3) of the plurality of differentially labeled compounds comprises an individually detectable label that does not undergo resonance energy transfer. The plurality of differentially labeled compounds further comprise a different base selected from A, T, G, and C, wherein each of the plurality of differentially labeled compounds that comprise a given base comprise an identical individually detectable label. The reaction is monitored to detect whether any of the differentially labeled compounds are incorporated into the nascent nucleic acid strand, where incorporation of one of the differentially labeled compounds is indicative of complementarity between a base in the differentially labeled compound and a position in the template nucleic acid being processed by the polymerase enzyme. Preferably, the detection of the incorporated labeled compounds occurs during the incorporation event, e.g., as the labeled compound is undergoing incorporation. In certain embodiments, the label portion of the labeled compound is not incorporated, e.g., is removed from the reactant portion during the incorporation event. In certain preferred embodiments, a plurality of incorporation events is monitored in real time to allow determination of a sequence of compounds so incorporated, e.g., a sequence of amino acids incorporated into a nascent polypeptide, or a sequence of nucleotides incorporated into a nascent polynucleotide. In certain embodiments, a single reaction being monitored is optically resolvable from other reactions being simultaneously monitored, e.g., on a single substrate or solid support. In some embodiments, an array of optically resolvable reaction sites is used to simultaneously monitor individual reactions.

In yet further aspects, methods are provided for distinguishing between binding of multiple reactants. In certain embodiments, such methods comprise providing a first reactant having a donor FRET chromophore and a second reactant comprising a first acceptor FRET chromophore, wherein the first acceptor FRET chromophore generates a first emission spectrum during binding to the first reactant. A third reactant comprising a second acceptor FRET chromophore is also provided, wherein the second acceptor FRET chromophore is identical to the first acceptor FRET chromophore, and further wherein the second acceptor FRET chromophore generates a second emission spectrum during binding to the first reactant, wherein the second emission spectrum is detectably distinct from the first emission spectrum. A reaction mixture is prepared comprising the first, second, and third reactants under conditions that promote binding of the second and third to the first reactant. Spectral emissions from the first reactant are monitored to detect binding of the second and/or third reactant to the first reactant. Detection of the first emission spectrum indicates binding of the second reactant to the first reactant; detection of the second emission spectrum indicates binding of the third reactant to the first reactant. In certain embodiments, at least one of the first and second emission spectra is a multi-spectrum emission spectrum. In certain embodiments, FRET efficiency between the donor FRET chromophore and the first acceptor FRET chromophore is different from FRET efficiency between the donor FRET chromophore and the second acceptor FRET chromophore. Preferably, the detection is performed in real time during the binding events and/or with single molecule/molecular complex resolution.

DETAILED DESCRIPTION OF THE INVENTION

Figure 1:
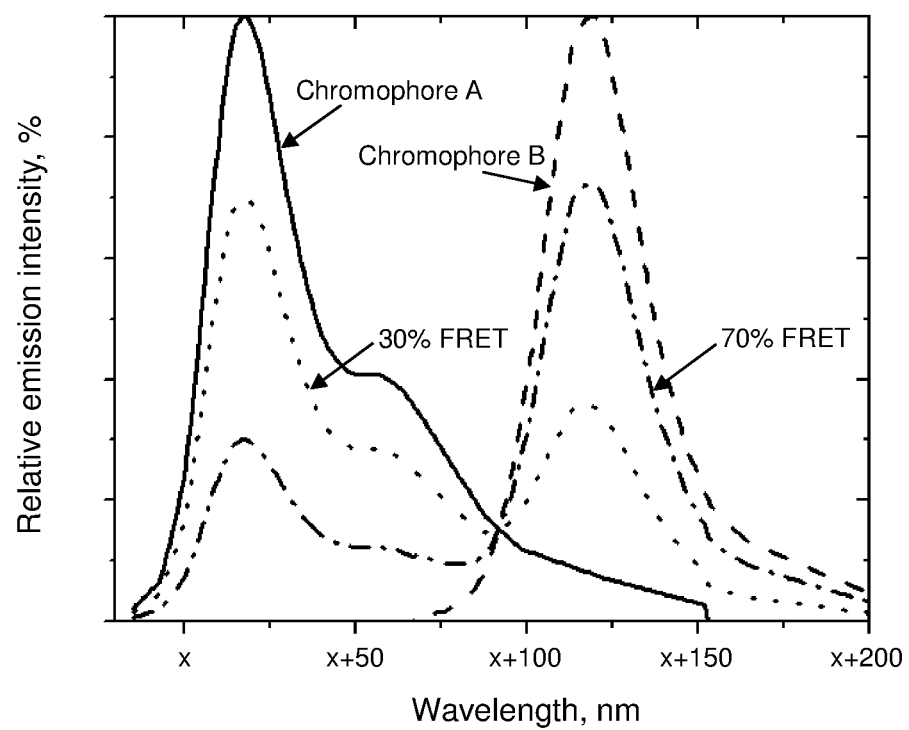
FIG. 1 an illustration of an exemplary profile for a set of four emission spectra according to certain embodiments of the invention.

The present invention is generally directed to labeled compounds, compositions containing such labeled compounds, and methods of use thereof, in particular in analytical reactions. In certain aspects, the present invention is directed to compounds comprising detectable labels that comprise a plurality of chromophores (e.g., fluorophores) that undergo Förster resonance energy transfer (FRET), and these labeled compounds are particularly useful in certain analytical reactions, e.g., for monitoring progress of the reaction, substrate processing, and/or product formation. In other aspects, the present invention is directed to compounds comprising detectable labels comprising at least one chromophore that undergoes FRET with at least one other chromophore on at least one other compound. In some aspects, the present invention is directed to analytical reactions comprising one or more labeled compounds that undergo intermolecular and/or intramolecular FRET. The use of excitation of chromophores and monitoring of their emissions are well known to those of skill in the art. Briefly, a chromophore in its excited state (e.g., due to exposure to excitation radiation/illumination) can emit energy to return to its ground state, and the emission spectra of a given chromophore has a set of characteristics (e.g., wavelength of peaks, intensity of peaks, number of peaks, shape of peaks, etc.) that can be used to detect the chromophore during an analytical reaction. When different chromophores are used to label different molecules, the emission spectrum that characterizes a particular chromophore can serve as a proxy for the presence of the particular molecule labeled therewith. A chromophore in its excited state can also transfer energy by a nonradiative, long-range dipole-dipole coupling mechanism to a second chromophore in close proximity, and this transfer is referred to as "FRET." This transfer is related to the overlapping spectra of the two chromophores, where the emission spectrum of the initially excited chromophore overlaps the absorption spectrum of the second chromophore so that there is energy transfer from the excited chromophore to the second chromophore. If the efficiency of the energy transfer is high (e.g., ~90-100%), the emission spectrum produced upon excitation of the two chromophores primarily comprises detectable emissions from the second chromophore.

Detectable labels that undergo FRET are termed "FRET labels" herein, and typically comprise at least two chromophores that engage in FRET such that at least a portion of the energy absorbed by at least one "donor chromophore," e.g., during excitation illumination, is transferred to at least one "acceptor chromophore," which emits at least a portion of the transferred energy as a detectable signal contributing to an emission spectrum. "FRET pair" refers to two chromophores that undergo FRET, e.g., one being the donor and one being the acceptor. A FRET label may comprise a single FRET pair, or multiple FRET pairs, as described elsewhere herein. In certain embodiments, a donor dye is excited with the laser source at its maximum absorbance wavelength, and an acceptor dye absorbs the emission from the donor with a given efficiency and emits the energy at a different wavelength, preferably a longer wavelength. It will be understood that the designations "donor chromophore" and "acceptor chromophore" are based on the direction of energy transfer between two chromophores, and in some embodiments, in particular those in which a FRET label comprises three or more chromophores, a single chromophore may serve as both a donor chromophore and an acceptor chromophore. For example, energy may be transferred from a first chromophore (donor) to a second chromophore (acceptor) that has a higher emission wavelength, and the second chromophore (now a donor) can pass energy onto a third chromophore (acceptor) with an even higher emission wavelength. FRET labels comprising more than two chromophores can be beneficial in various ways. For example, their use can increase the difference in the excitation/absorption wavelength and the observed emission wavelength, which can reduce interference of the excitation radiation with measurement of the emission spectrum. Further, use of a FRET label comprising greater than two chromophores allows greater flexibility in generating a set of distinctive and unique emission spectra from different FRET labels comprising the same set of chromophores, as described below. Although certain preferred embodiments focus on FRET labels on a single labeled compound, it is to be understood that different chromophores of a FRET label may also reside on different labeled compounds, e.g., resulting in energy transfer when the two or more labeled compounds interact in a way that brings the chromophores close enough to one another to allow energy transfer, e.g., during a binding and/or complex formation.

In certain aspects, the chromophores in a FRET label, e.g., in a labeled compound, are configured to achieve a desired efficiency of the energy transfer ("FRET efficiency") between the donor and acceptor chromophores, where the desired FRET efficiency is chosen to ensure a desired emission intensity (or range thereof) at one or more emission wavelengths in the emission spectrum. As used herein, "emission intensity" refers to the intensity of emitted signal at a given wavelength, and can generally be related to the height of a peak in an emission spectrum graph, where a relatively higher peak is indicative of a higher emission intensity and a relatively lower peak is indicative of a lower emission intensity. FRET efficiency (E) generally refers to the loss in intensity of the donor chromophore emission in the presence of the acceptor chromophore, and can be expressed using the following equation:

$$E=1-Q_{da}/Q_d,$$

where $Q_{da}$ is the fluorescence intensity of the donor in the presence of the acceptor and $Q_d$ is the fluorescence intensity of the donor in the absence of the acceptor. Essentially, the equation provides the fraction of donor fluorescence that is transferred to the acceptor fluorophore.

A desired FRET efficiency, as used herein, is the calculated FRET efficiency based upon the configuration of a FRET label, e.g. within a labeled compound or in a complex comprising multiple labeled compounds, and it will readily be understood that in practice the experimental FRET efficiency may vary somewhat from the desired FRET efficiency. For example, in some cases, a FRET label configured to have a desired FRET efficiency experimentally produces an emission spectrum having a small range of FRET efficiencies, e.g., within about 15%, or more preferably within about 10%, or even more preferably within about 5%, 3%, 2%, or 1% of the desired FRET efficiency. As such, a configuration of chromophores chosen to achieve a desired FRET efficiency does not necessarily mean that the FRET efficiency achieved in a given assay will be exactly the desired efficiency, but that the experimental FRET efficiency may vary somewhat within a range around the desired FRET efficiency. As such, the actual emission intensities achieved with a given molecular configuration may also vary somewhat from the desired emission intensities computed based upon a desired FRET efficiency as the actual emission intensities in an emission spectrum are dependent upon the actual range of FRET efficiencies achieved in a given experiment. In practice, such minor variations in FRET efficiencies are not typically problematic. Where multiple labeled compounds are present in a single analytical reaction they are designed to have distinguishable emission spectra even in the presence of minor variations in FRET efficiency. The emission spectra of multiple labeled compounds can also be compared to one another to confirm the identity of a given labeled compound or association between two or more labeled compounds in the reaction. For example, in some cases the relative emission intensities at various wavelengths compared between emission spectra are more informative in identifying the source of a particular emission spectrum than the absolute emission intensities that characterize it.

In certain preferred embodiments, the configuration of the chromophores (e.g., spacing between them) in the compound or complex determines the FRET efficiency, and therefore the emission spectrum. For example, in some FRET labels a spacing of about 2 nm allows very high FRET efficiency, while a spacing of about 9 nm results in a relatively low FRET efficiency. Other factors that influence FRET efficiency include the spectral overlap of the donor emission spectrum and the acceptor absorption spectrum, and the relative orientation of the donor emission dipole moment and the acceptor absorption dipole moment. This information is available to the ordinary practioner for a large variety of chromophores, allowing substantial flexibility in choosing FRET labels for various applications of the instant invention.

In certain embodiments in which the FRET efficiency is less than 100%, at least two chromophores in a FRET label emit detectable signals that contribute to the resulting multispectral emission spectrum, e.g., represented by at least two "peaks" characterized by their wavelength and intensity. In general, as the FRET efficiency increases, the emission intensity at the donor chromophore's emission wavelength decreases and the emission intensity at the acceptor chromophore's emission wavelength increases. As such, two FRET labels that each comprise the same set of chromophores can have distinct emission spectra if each is configured to ensure a distinct FRET efficiency or range thereof. For example, if a first FRET label has a higher FRET efficiency than a second FRET label, the emission spectrum corresponding to the first FRET label will have a relatively lower intensity peak at the emission wavelength of the donor chromophore and a relatively higher intensity peak at the emission wavelength of the acceptor chromophore than does the second FRET label. For example, the intensity of the first FRET label at the emission wavelength of the donor chromophore may be less than 90%, 80%, 70%, 60%, 50%, 40%, 30%, 20%, 10%, or 5% of that of the second FRET label; and the intensity of the second FRET label at the emission wavelength of the acceptor chromophore may be less than 90%, 80%, 70%, 60%, 50%, 40%, 30%, 20%, 10%, or 5% of that of the first FRET label. The differences between emission intensities at donor or acceptor emission wavelengths for two different FRET labels can also be expressed as ratios of the intensities for each label, e.g., 10:1, 8:1, 6:1, 4:1, 3:1, 2:1, 1:2, 1:3, 1:4, 1:6, 1:8, or 1:10 at a given wavelength. In this way, FRET labels comprising the same set of chromophores can be configured such that each has a distinctive emission spectra based at least on emission intensities, even if emission wavelengths are the same. In certain aspects, a single FRET pair may be used to provide at least about 2-10 different emission spectra based on the orientation of the chromophores relative to one another. Further, FRET labels having more than two chromophores can provide even more different emission spectra based on the orientation of the chromophores with respect to one another, and therefore the relative FRET efficiencies of each transfer event within the label.

Of particular interest is the structure within the labeled compounds (e.g., linker(s)) that maintains the proper configuration of the chromophores to result in a desired FRET efficiency (and therefore emission spectrum) with no or only a minimum of undesirable effects to the analytical reaction under examination. As is well known in the art, the efficiency (E) of the transfer of the excitation energy from the donor to the acceptor depends on the donor-to-acceptor separation distance r with an inverse $6^{th}$ power law due to the dipole-dipole coupling mechanism: $E=1/[(1+(r/R_0)^6]$, where r is the distance between the donor and acceptor and $R_0$ is the Förster distance of the donor and acceptor pair at which the FRET efficiency is 50%. The efficiency rapidly increases to 100% as the separation distance decreases below $R_0$, and conversely, decreases to zero when r is greater than $R_0$. (For a review of FRET microscopy, see, for example, www[dot]olympusfluoview[dot]com/applications/fretintro[dot]html (where "[dot]" indicates a period in the web address), which is incorporated herein by reference in its entirety for all purposes.) When r is approximately 50% of $R_0$, the resonance energy transfer efficiency is near the maximum. When the donor-acceptor distance exceeds the $R_0$ value by 50%, the slope of the curve is so shallow that longer separation distances are not resolved. Alternatively, when the donor and acceptor radius (r) equals the Förster distance, then the transfer efficiency is 50%. At this separation radius, half of the donor excitation energy is transferred to the acceptor via resonance energy transfer, while the other half is dissipated through a combination of all the other available processes, including fluorescence emission. Thus, an appropriate length of r can be used to modulate the energy transfer efficiency and thus create a unique emission spectrum.

FRET labels with multi-spectral properties can be used alone, e.g., on a single labeled compound or on multiple interacting labeled compounds; with other FRET labels having multi-spectral properties; with other FRET labels not having multi-spectral properties; with non-FRET labels; or a combination thereof, e.g., in a single analytical reaction. Non-FRET labels used with FRET labels may comprise the same or different chromophores as the FRET labels, as long as the presence of the chromophore in the non-FRET labels does not interfere with the energy transfer within the FRET labels. Emission spectra from different labels in a single analytical reaction can be distinguished using various criteria including, but not limited to, emission wavelength(s), emission intensity(s), spectral shape, or a combination thereof. As described above, differences in emission intensity at a given wavelength for different FRET labels can also be expressed in terms of percent differences or ratios. Detailed descriptions of certain examples of criteria for distinguishing emission spectra are provided in U.S. Patent Publication No. 2009/0024331, the disclosure of which is incorporated herein by reference in its entirety for all purposes. Alternate labeling strategies that can also be used with the methods and compositions described herein include those provided in U.S. Patent Publication No. 2009/0208957, which is incorporated herein by reference in its entirety for all purposes.

In certain aspects, a composition of the invention comprises a plurality of FRET-labeled compounds in a single analytical reaction. In preferred embodiments, the configuration and/or types of the chromophores in each compound results in the production of distinctive emission spectra, wherein each FRET-labeled compound has an emission spectrum that is distinguishable from the emission spectrum of every other FRET-labeled compound in the analytical reaction, thereby enabling unambiguous identification of each FRET-labeled compound. In certain embodiments, the multiple different labeled compounds comprise the same set of chromophores, but have a different configuration and therefore different emission spectra based at least in part on different FRET efficiencies resulting in variations in emission intensity at one or more wavelengths and, in certain preferred embodiments, not due to a change in the emission wavelength(s). In other words, two or more different emission spectra can comprise the same number of peaks at the same wavelengths, but still be distinct from one another based on the emission intensity at those peaks rather than the emission wavelengths at which the peaks are present. In other embodiments, multiple different labeled compounds can comprise different sets of chromophores, and their different emission spectra can be distinguished based at least in part on variations in emission wavelengths and/or emission intensities. In certain embodiments, multiple different labeled compounds comprise some, but not all, of the same chromophores. For example, a single reaction mixture can contain a first labeled compound comprising a FRET label consisting of two chromophores, and a second labeled compound comprising the two chromophores in the first labeled compound and a third chromophore that serves as an acceptor for the emission from the first two chromophores, emitting at an additional or different emission wavelength. In some such embodiments, the emission spectra from the first and second labeled compounds may be distinguished not only by changes in intensity at emission wavelengths corresponding to the first two chromophores, but also by the existence of a third emission wavelength in the emission spectra of the second labeled compound. Additional, optically distinctive labels can be designed by changing the conformation of the first and second FRET labels to change the FRET efficiency within the two chromophores in the first label or between the three chromophores in the second label.

In some aspects, the compositions of the invention can further comprise non-FRET-labeled compounds that have emission spectra that are distinct from the emission spectra of the FRET-labeled compounds of the invention. In some embodiments, a single labeled compound can comprise both a FRET label and a non-FRET label, where the non-FRET label has an emission spectrum that is independent of the FRET label. In certain embodiments, FRET-labeled compounds may be combined with non-FRET-labeled compounds (e.g., comprising one or more chromophores) in a single analytical reaction, with identification of the reactive portion of the labeled compound based at least in part on a comparison of the emission spectra generated from the label portions. For example, a first labeled compound can be labeled with chromophore A, a second labeled compound can be labeled with chromophore B, a third labeled compound can be labeled with the A-B FRET pair in a first orientation that results in 30% FRET efficiency, and a fourth labeled compound can be labeled with the A-B FRET pair in a second orientation that results in 70% FRET efficiency. An prophetic graphical representation of the various emission spectra that can result from these four different labeled compounds is provided in FIG. 1. The labeled compound labeled with only chromophore A ("Chromophore A") produces a single peak of 100% relative emission intensity at a first wavelength and the labeled compound labeled with only chromophore B ("Chromophore B") produces a peak of 100% relative emission intensity at a second wavelength. The labeled compound labeled with the FRET pair having 30% FRET efficiency ("30% FRET") produces two peaks, one of relatively high emission intensity (~70% relative emission intensity) at the first wavelength and one of relatively low emission intensity (~35% relative emission intensity) at the second wavelength. The labeled compound labeled with the FRET pair having 70% FRET efficiency ("70% FRET") produces two peaks, one of relatively low emission intensity (~30% relative emission intensity) at the first wavelength and one of relatively high emission intensity (~72% relative emission intensity) at the second wavelength. These four prophetic emission spectra are easily distinguishable from one another, thereby allowing the ordinary practitioner to unambiguously identify the labeled compound, and in particular the reactive portion thereof, by virtue of the characteristics of a detected emission spectrum. In this way, four different emission spectra are produced in a single analytical reaction using only two chromophores, two of the emission spectra being produced from FRET pairs having different conformations and therefore different FRET efficiencies, and two of the emission spectra being produced from non-FRET labels comprising only one of the chromophores in the FRET pairs.

In certain aspects, the present invention is directed to labeled compounds useful as analogs to naturally occurring reaction components in analytical reactions, including but not limited to, binding assays (e.g., antibody assays), nucleic acid sequencing, protein sequencing, methylation mapping, secondary structure analysis, enzyme assays, kinetic studies, assays that monitor conformation changes of macromolecules or macromolecular complexes, and the like. For example, the FRET labels of the invention can be used to differentially label tRNA molecules during translation in order to determine the sequence of amino acids incorporated into a nascent polypeptide chain, to detect binding of a ligand to a receptor, to measure antigen binding to an antibody, to monitor the rate of an enzymatic reaction, and to determine the sequence of polymers during synthesis. In certain preferred embodiments, at least one reaction component, labeled or unlabeled, is immobilized or otherwise confined at a reaction site that is monitored for the presence of labeled reactants. In certain preferred embodiments, a single reaction site is optically resolvable from other reaction sites in an analytical reaction such that a single molecule of a labeled compound can be detected and distinguished from other labeled compounds present in the reaction. Such analytical reactions may comprise labeled components having intramolecular FRET labels, intermolecular FRET labels, non-FRET labels, or combinations thereof. Certain embodiments of such analytical reactions are provided in U.S. provisional application No. 61/186,661, filed Jun. 12, 2009; U.S. provisional application No. 61/186,645, filed Jun. 12, 2009; and U.S. Ser. No. 12/635,618, filed Dec. 10, 2009, the disclosures of which are incorporated herein by reference in their entireties for all purposes.

In certain embodiments, the present invention is directed to labeled compounds useful as analogs to naturally occurring nucleoside triphosphates or previously described analogs in a variety of different applications, including particularly, analytical nucleic acid analyses such as genotyping, sequencing, and other characterization and identification analyses. For example, in certain embodiments a nucleotide analog is a nucleotide tetraphosphate, a nucleotide pentaphosphate, a nucleotide hexaphosphate, a nucleotide septaphosphate, or a nucleotide octophosphate. In preferred embodiments, the labeled compounds are used in template-directed sequencing reactions and their incorporation into a nascent nucleic acid strand (e.g., DNA or RNA strand) is monitored in real-time. In some embodiments, all nucleotide analogs in an analytical reaction are FRET-labeled compounds. In other embodiments, a first subset of nucleotide analogs are labeled with FRET-labels and a second subset of nucleotide analogs are labeled with non-FRET-labels in a single analytical reaction, e.g., a template-directed sequencing reaction. In some embodiments, a single nucleotide analogs is labeled with both a FRET label and a non-FRET label. For example, a sequencing reaction may comprise two different nucleotide analogs labeled with FRET labels having the same FRET pair but different FRET efficiencies, and the other two nucleotide analogs each labeled with a different one of the chromophores that make up the FRET pair in the FRET-labeled nucleotide analogs. As such, only two chromophores would be required to differentially label four different nucleotide analogs, two with FRET labels and two with non-FRET labels. Therefore, two chromophores can be used to generate four distinct emission spectra in an analytical reaction. In some embodiments, more than one FRET-labeled nucleotide analog in a reaction has at least one or two chromophores in common. In some embodiments, chromophores in a FRET-labeled compound are fluorophores.

The compounds and methods herein may further comprise various aspects of the following patent applications and patents: U.S. Ser. No. 61/069,247, filed Mar. 13, 2008; U.S. Ser. No. 12/241,809, filed May 15, 2008; U.S. Pub. No. 2008/0241866 A1; U.S. Pat. Nos. 7,405,281; 7,056,676; and 5,688,648, all of which are incorporated herein by reference in their entireties for all purposes.

I. Compounds

In certain aspects, the present invention is directed to FRET-labeled compounds comprising at least two chromophores and uses thereof. In certain aspects, the labeled compound is configured to provide submaximal FRET efficiency upon excitation illumination, and this submaximal FRET efficiency is chosen to promote production of a desired emission intensity at one or more emission wavelengths that is detectably different than that produced when FRET efficiency is maximized, as further described elsewhere herein. For example, the distance between the chromophores in the FRET label can be chosen to provide a desired FRET efficiency upon excitation illumination, and this distance will produce a distinct and identifiable emission spectra (e.g., a multi-spectral emission spectra where emissions at two or more different wavelengths are detectable) based in part of the emission intensities at the emission wavelengths of both the donor and acceptor chromophores. As such, the conformation of the labeled compounds, and in particular the orientation of the chromophores with respect to each other, is of particular interest. For purposes of description, the labeled compound comprises a label portion and a reactant portion, the reactant portion denoting the portion of the labeled compound that serves as the reactant in the reaction of interest, with or without the label group. For example, in nucleic acid reactions utilizing fluorescently labeled nucleotide analogs as the labeled compound, the label portion that includes the fluorescent dye component(s) is connected to the reactant portion comprising a nucleotide analog. As used herein, the term "nucleotide analog" refers generally to nucleosides, nucleotides, and analogs and derivatives thereof. In describing certain labeled compounds of the invention as nucleotide analogs, it is meant that in a particular application, the compounds or compositions function in a manner similar to or analogous to naturally occurring nucleoside triphosphates (or nucleotides), and does not otherwise denote any particular structure to such compounds. For example, in certain embodiments a nucleotide analog for use as a labeled compound of the invention comprises a polyphosphate with at least 2, 3, 4, 5, 6, 7, 8, 9, or 10 phosphate groups. Similarly, for a binding assay, a first binding partner may be immobilized on a surface and a second binding partner that specifically associates with the first binding partner can comprise a label portion that includes the fluorescent dye component(s) connected to a reactant portion comprising a ligand for the first binding partner. In some such embodiments, the first binding partner also comprises a FRET or non-FRET label portion. In certain embodiments, FRET occurs between a label portion on the first binding partner and a label portion on a second binding partner. Such binding partners include, e.g., antibodies and antigens, receptors and ligands, enzymes and substrates, complementary nucleic acid molecules, nucleic acid binding sites and proteins that bind to them (e.g., histones, transcription factors, etc.), and the like.

Typically, a labeled compound of the invention is configured to ensure a desired FRET efficiency (or range thereof) between at least two chromophores such that, upon excitation illumination, a distinctive and identifiable emission spectrum is generated based upon emission intensity at one or more emission wavelengths. In preferred embodiments, multiple compounds labeled with the same set of chromophores (e.g., FRET pair) are configured such that each has a unique orientation of the chromophores with respect to one another, resulting in the production of distinctive and identifiable emission spectra for each labeled compound. Typically, the label portion of such labeled compounds provides linkage between the chromophores of sufficient lengths and rigidities to maintain the desired orientation of the chromophores with respect to one another (e.g., during an analytical reaction) such that a distinct emission spectrum will be reliably produced upon excitation illumination.

In a first aspect, the maintenance of the desired relative orientation of the chromophores (e.g., distance between them) may be characterized as a function of the desired reduction in maximal FRET efficiency upon excitation illumination as compared to similar molecules in which the orientation is selected to optimize FRET efficiency. Put another way, a range of distances between the donor and acceptor chromophores can be chosen to ensure inefficient energy transfer (and therefore submaximal FRET efficiencies), which produce distinct emission spectra that typically include peaks at wavelengths corresponding to both donor and acceptor emission wavelengths. For example, the chromophores may be oriented to have a FRET efficiency that is about 0%, 5%, 10%, 15%, 20%, 25%, 30%, 35%, 40%, 45%, 50%, 55%, 60%, 65%, 70%, 75%, 80%, 85%, 90%, or 95% of the maximal FRET efficiency between a set of chromophores were they oriented to maximize energy transfer between the chromophores. In a simple, ideal, two-chromophore FRET label, a configuration that ensured 0% FRET efficiency would result in no energy transfer between donor and acceptor chromophores, so the emission intensities and wavelengths would depend on how well the excitation illumination can excite each chromophore independently and what the resulting emission would be from each. Typically, a peak of high intensity would be produced by emission from the donor chromophore, and no peak (or a very small peak) would be produced by emission from the acceptor chromophore, e.g., where excitation illumination was of a wavelength that excited the donor but not the acceptor. A configuration that promoted 100% FRET efficiency would result in complete transmission of all excitation energy from the donor chromophore to the acceptor chromophore, so the emission spectra would only contain signal resulting from emission from the acceptor chromophore. A configuration that promoted 50% FRET efficiency would result in the intensity of the donor emission being reduced by half, and a resulting increase in the intensity of the acceptor, resulting in an emission spectrum comprising significant emission signal from both the donor and acceptor. In this way, the orientation of the chromophores can be adjusted to achieve a desired FRET efficiency for a given FRET label.

FRET-labels comprising more than two chromophores are capable of producing more complex emission spectra, depending on the FRET efficiency between each pair of chromophores between which energy transfer occurs. In some embodiments, the FRET labels are designed to allow some level of emission from all chromophores to contribute to the emission spectrum, and in other embodiments the labels are designed to restrict detectable emission to only a subset of chromophores. The FRET efficiency between each pair of chromophores undergoing energy transfer can be the same or can differ within a single FRET label. As such, in a three-chromophore FRET label, the FRET efficiency between a first and second chromophore can be the same or different from the FRET efficiency between the second chromophore and a third chromophore. As will be clear to one of ordinary skill in the art, the number of chromophores and FRET efficiency between them can be adjusted to provide a vast number of distinct and identifiable emission spectra by virtue of the resulting emission intensities, even when each emission spectrum includes peaks at one or more of the same wavelengths. As such, in some preferred applications, a plurality of multiple emission intensities at a plurality of emission wavelengths allows the various labeled compounds in a reaction to be reliably distinguished from one another.

In another aspect, the labeled compounds of the invention are characterized by the specific distances provided between the chromophores (e.g., in a FRET pair) in the label portion of a single labeled compound or within a complex comprising multiple labeled compounds. Because of differences in the relative flexibility of different linkages, such distances are generally stated in terms of an operating or functional distance, e.g., the average maintained distance between the chromophores. In the case of linear linkages, such distances may be provided using polymers or other linear structures that have persistence lengths of the desired distances. Alternatively, some linkages may provide a spatial separation based upon the volume of the linkage, e.g., PEG linkers may exist as a random coil and polyproline forms a type II trans helix, both of which can provide a relatively consistent spatial separation between the chromophores.

While precise distances or separation may be varied for different reaction systems to obtain optimal results, in many cases it will be desirable to provide a linkage that maintains a distance of about 2-8 nm between chromophores in a FRET pair. The specific spacing between the chromophores will vary depending on the chromophores used and the desired FRET efficiency (0-100%).

A number of linkers may be employed that will provide the desired conformation of the FRET label chromophores within a labeled compound or complex of multiple labeled compounds, e.g., including the separation between chromophores in a FRET pair, the distance between a chromophore of a FRET pair and a reactant portion, or the distance between a chromophore in a first labeled compound and a chromophore in a second labeled compound when the first and second compounds are bound to or otherwise associated with one another. In general, a linker comprising one or more chromophores can be linear or branched, and multiple linkers may be utilized in a single labeled compound. For example, a single linker may be bound to the terminal phosphate of a nucleotide analog, and this linker may branch into two arms, wherein each arm comprises a single chromophore of a FRET pair, and wherein the orientation of the two arms ensures a given distance between the two chromophores, thereby ensuring a desired FRET efficiency upon excitation illumination. In other embodiments, a linear linker may contain both chromophores, with the portion of the linker between them designed to ensure a given orientation between them, and therefore a desired FRET efficiency. In yet further embodiments, multiple linear and/or branched linkers may be bound to different portions of a polyphosphate chain extending from the nucleotide analog, and each of these may comprise one or more chromophores in a desired orientation.

A wide variety of linkers and linker chemistries are known in the art of synthetic chemistry and may be employed in constructing the label portions and coupling them to the reactant portions of the compounds of the invention. For example, such linkers may include organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, alkyl, e.g., alkane, alkene, alkyne alkoxy or alkenyl, or ethylene glycol linkers are used. Some examples of linkers are described in Published U.S. Patent Application No. 2004/0241716; U.S. Ser. No. 61/069,247, filed Mar. 13, 2008; and U.S. Patent Publication No. 2009/0233302, all of which are incorporated herein by reference in their entireties for all purposes. Additionally, such linkers may be selectively cleavable linkers, e.g., photo- or chemically cleavable linkers or the like, many types of which are known by those of ordinary skill in the art.

In certain embodiments alkyl linkers may be used to provide a useful distance between the chromophores. For example, longer amino-alkyl linkers, e.g., amino-hexyl linkers, are generally sufficiently rigid to maintain a desired spacing. In certain aspects providing linkers with desired functional lengths can involve the use of more rigid chemical structures in such linkers. Typically, such rigid structures include laterally rigid chemical groups, e.g., ring structures such as aromatic compounds, multiple chemical bonds between adjacent groups, e.g., double or triple bonds, in order to prevent rotation of groups relative to each other, and the consequent flexibility that imparts to the overall linker. Alternatively or additionally, secondary chemical structures may be used to impart rigidity, including, for example helical structures, sheet structures, and the like, as well as structures that employ cooperative molecules in providing rigidity, e.g., complementary molecular structures. Other examples of the linkers of the invention include oligopeptide linkers, and in particular, oligoproline or polyproline linkers that include ring structures. (See, e.g., Schuler, B. (2005) Proc. Natl. Acad. Sci. 102(8):2754-2759, incorporated by reference herein in its entirety for all purposes.)

As noted, some linkers according to the invention derive rigidity through the internal chemical structure of the linker molecules. For example, linker molecules may derive their rigidity through a reduction in the number of single bonds that can yield points of rotation, and thus, flexibility in the linker. As such, the linkers will typically comprise double bonds, triple bonds or ring structures, which will provide the increased rigidity. Examples of double and/or triple bonded linker structures include, for example, conjugated alkynes, conjugated alkenes, aryl alkynes, and the like. While illustrated as polymeric structures of repeating monomeric subunits, it will be appreciated that the linkers of the invention may comprise mixed polymers of differing monomeric subunits.

The linkers used in the context of the invention may additionally or alternatively derive rigidity from secondary, tertiary, or even quaternary structures. For example, in some cases, polypeptide linkers may be employed that have helical or other rigid structures. Such polypeptides may be comprised of rigid monomers, e.g., as in the oligoproline or polyproline linkers noted above, which derive rigidity both from their primary structure, as well as from their helical secondary structures, or may be comprised of other amino acids or amino acid combinations or sequences that impart rigid secondary or tertiary structures, such as helices, fibrils, sheets, or the like. By way of example, polypeptide fragments of structured rigid proteins, such as fibrin, collagen, tubulin, and the like may be employed as rigid linker molecules.

In a related aspect, double-stranded nucleic acids can be used to provide both the requisite length and rigidity as a linker. Similarly, related structures, such as double-stranded peptide nucleic acids (PNAs) or DNA/PNA hybrid molecules may be employed as the linkers. By way of illustration, the persistence length of double-stranded nucleic acids, i.e., the length up to which the structure behaves more rod-like than rope-like, is approximately 50 nm, allowing for facile construction of rigid linkers up to and even beyond this length. In certain preferred aspects, a nucleic acid linker that comprises a double-stranded portion to impart rigidity is used as a linker group, e.g., between the chromophores or between one or more chromophores and the reactant portion of the labeled compound. Such double-stranded nucleic acids may comprise distinct but complementary nucleic acid strands that are hybridized together, where one or both strands bear a chromophore. Alternatively, the nucleic acid linker may comprise a single molecule with complementary portions, such that the molecule self hybridizes to form a hairpin loop structure, where the label component is provided at a point on the loop, distal to the reactant portion. The use of nucleic acid linker structures provides advantages of ease of synthesis of the labeled linker, using conventional DNA synthesis and dye coupling techniques, and resultant control of linker length, e.g., approximately 0.3 nm of distance imparted for each added monomer in the linker portion. Consequently, one can easily adjust the length of the linker to accommodate various spacing between the chromophores and the reactant portion, or between the chromophores themselves. Additionally, the ability to adjust the rigidity of the linker, in real time provides interesting reaction control elements, e.g., by adjusting the integrity of the hairpin structure by modifying the hybridization conditions for the linker, e.g., adjusting salt, temperature, or the like. These linkers are also readily coupled to nucleotide analogs, whether coupled through groups on the nucleobase, the ribosyl moiety, or through one of the phosphate groups (e.g., alpha, beta, gamma, or others in the case of tetra, penta, or hexa phosphate analogs, or others). Further description of such nucleic acid linkers is provided, e.g., in U.S. Ser. No. 61/069,247, filed Mar. 13, 2008 and U.S. Patent Publication No. 2009/0233302, both of which are incorporated herein by reference in their entireties for all purposes.

In certain aspects, the label portion of a labeled compound comprises at least one detectable labeling moiety, or more than one detectable labeling moiety, and in certain preferred embodiments, and as described above, the label portion of a labeled compound comprises at least two detectable labeling moieties that preferably can form a FRET pair coupled to the reactant portion via at least one linking group. Detectable labeling moieties generally denote chemical moieties that provide a basis for detection and identification of the reactant portion of the labeled compound. In preferred aspects, the detectable labeling moieties comprise optically detectable moieties, including luminescent, chemiluminescent, fluorescent, fluorogenic, chromophoric and/or chromogenic moieties (with fluorescent and/or fluorogenic labels being particularly preferred), but such labels may also impart additional properties to the labeled compounds of the invention, e.g., a detectable electrical or electrochemical property, or a different physical or spatial property. A multitude of labeling moieties is known to those of ordinary skill in the art, some of which are described herein.

Chromophores useful with the compounds, compositions, and methods of the invention may be fluorescent dyes, non-fluorescent dyes, or the like. Examples of suitable chromophores include, but are not limited to, fluorescein and its derivatives, rhodamine-based dyes, and the cyanine-based dyes such as isothiocyanines, merocyanines, indocarbocyanines (e.g., Cy3 and Cy3.5), indodicarbocyanines (e.g., Cy5 and Cy5.5), indotricarbocyanines (e.g., Cy7), thiazole orange, oxazole yellow, the Alexa® dyes (e.g., Alexa 488, 555, 568, 647, and 660), CYA (3-(epsilon-carboxy-pentyl)-3'ethyl-5,5'dimethyloxacarbocyanine), and the like (see Mujumdar, et al Bioconjugate Chem. 4(2):105-111, 1993; Ernst, et al, Cytometry 10:3-10, 1989; Mujumdar, et al, Cytometry 10:1119, 1989; Southwick, et al, Cytometry 11:418-430, 1990; Hung, et al, Anal. Biochem. 243(1):15-27, 1996; Nucleic Acids Res. 20(11):2803-2812, 1992; Mujumdar, et al, Bioconjugate Chem. 7:356-362, 1996; Southwick and Waggoner, U.S. Pat. No. 4,981,977, issued Jan. 1, 1991, all of which are incorporated herein by reference in their entireties for all purposes). These and other such chromophores are readily commercially available, e.g., from the Amersham Biosciences division of GE Healthcare, and Molecular Probes/Invitrogen/Life Technologies Inc. (Carlsbad, Calif.)., and are described in 'The Handbook—A Guide to Fluorescent Probes and Labeling Technologies, Tenth Edition' (2005) (available from Invitrogen, Inc./Molecular Probes/Life Technologies, and incorporated herein by reference in its entirety for all purposes). A variety of other fluorescent and fluorogenic labels for use with nucleoside polyphosphates, and which would be applicable to the compounds of the present invention are described in, e.g., Published U.S. Patent Application No. 2003/0124576, the full disclosure of which is incorporated herein in its entirety for all purposes. In certain preferred embodiments, the chromophores in a FRET pair are fluorophores.

Any of a number of fluorophore combinations can be selected for use in the present invention (see for example, Pesce et al., eds, Fluorescence Spectroscopy, Marcel Dekker, New York, 1971; White et al., Fluorescence Analysis: A practical Approach, Marcel Dekker, New York, 1970; Handbook of Fluorescent Probes and Research Chemicals, 6th Ed, Molecular Probes, Inc., Eugene, Oreg., 1996; which are incorporated herein by reference reference in their entireties for all purposes). In general, a preferred donor fluorophore is selected that has a substantial spectrum of the acceptor fluorophore. Furthermore, it may also be desirable in certain applications that the donor have an excitation maximum near a laser frequency such as Helium-Cadmium 442 nM, Argon 488 nM, Nd:YAG 532 nm, He—Ne 633 nm, etc. In such applications the use of intense laser light can serve as an effective means to excite the donor fluorophore. In certain preferred embodiments, the acceptor fluorophore has a substantial overlap of its excitation spectrum with the emission spectrum of the donor fluorophore. In some cases, the wavelength maximum of the emission spectrum of the acceptor moiety is preferably at least 10 nm greater than the wavelength maximum of the excitation spectrum of the donor moiety. Additional examples of useful FRET labels include, e.g., those described in U.S. Pat. Nos. 5,654,419, 5,688,648, 5,853,992, 5,863,727, 5,945,526, 6,008,373, 6,150,107, 6,177,249, 6,335,440, 6,348, 596, 6,479,303, 6,545,164, 6,849,745, 6,696,255, and 6,908,769 and Published U.S. Patent Application Nos. 2002/0168641, 2003/0143594, and 2004/0076979, the disclosures of which are incorporated herein by reference for all purposes.

As noted previously, the linkage between the chromophores in a FRET label is configured to provide sufficient linker length and structure so as to maintain a sufficient distance between the chromophores, e.g. during detection, thereby ensuring a predictable and distinctive emission spectrum upon excitation illumination. As noted elsewhere herein, many different kinds of analytical reactions can benefit from the use of the FRET labels of the present invention, and the most benefit is typically found in those analytical reactions in which multiple reactants are to be differentially labeled. For example, in the context of nucleic acid (e.g., DNA or RNA) sequencing that employs real-time detection of the interaction of labeled nucleotides with polymerase enzymes (e.g., DNA polymerases, RNA polymerases, reverse transcriptases, etc.), one object of the instant invention is to use the same FRET label to unambiguously identify multiple different labeled compounds in the reaction based on differences in emission spectra related to differences in orientation (e.g., spacing) of the chromophores in the labeled compounds. This is a benefit to the ordinary practitioner because it allows the use of fewer chromophores to detect the same number of compounds, which provides flexibility in designing the analytical reaction. For example, a chromophore that has been shown to negatively impact the quality of an analytical reaction (e.g., by lowering duration, processivity, or fidelity; by damaging reaction components; by having a short half-life in the analytical reaction; etc.) may be omitted in favor of using a FRET label comprising chromophores with fewer undesirable properties. Likewise, fewer chromophores can be used to label multiple tRNAs during protein translation, or to label multiple ligands to a given receptor in a binding assay. Other applications of the compositions and methods provided herein will be clear to those of ordinary skill in the art based upon the teachings provided herein.

The use of FRET labels allows for a high degree of flexibility in choosing the excitation and emission spectra for the labeled compounds of the invention, and provides particular advantages for differentially labeling various components of an analytical reaction. For example, in certain embodiments across a variety of different compounds, one can utilize a single type of donor chromophore that has a single excitation wavelength, but couple it with multiple different acceptor chromophores (e.g., having an excitation wavelength that at least partially overlaps with the emission spectrum of the donor), where each different acceptor chromophore has an identifiably different emission spectrum. The donor chromophore may be on the same or a different reactant as the acceptor chromophore. For example, in some embodiments the donor chromophore is immobilized at a reaction site or is attached to a reactant that interacts with multiple other reaction components, each of which can carry a detectably different acceptor chromophore. Alternatively, different donor chromophores whose emission spectra overlap may be coupled with different acceptor chromophores. In alternative embodiments, the donor and acceptor chromophores are the same for multiple labeled compounds, but the conformation of the labeled compound varies, resulting in a different FRET efficiency for each pair of chromophores in each labeled compound. The emission spectra from each FRET label can thereby be distinctive from every other, e.g., based on emission intensity at a plurality of emission wavelengths, as described above. For example, consider two labeled compounds, both with the same FRET pair comprising a donor chromophore that emits at a first wavelength and an acceptor chromophore that emits at a second wavelength, where the conformation of the first labeled compound results in a FRET efficiency of 25% and the configuration of the second labeled compound results in a FRET efficiency of 75%. Under excitation illumination the FRET pair in the first labeled compound would produce an emission spectrum with a large peak (high emission intensity) at the first wavelength and a small peak (low emission intensity) at the second wavelength, while the FRET pair in the second labeled compound would produce an emission spectrum with a small peak at the first wavelength and a large peak at the second wavelength. As such, even though both emission spectra comprise peaks at both the first and second wavelengths, these two emission spectra are distinguishable from one another, thereby allowing identification of the reactant portion of the labeled compound. Likewise, the same two chromophores can be used in additional labeled compounds having different FRET efficiencies that result in spectra that are distinguishable from those of the first and second labeled compounds, for example a FRET efficiency that results in comparable peaks at the two wavelengths. In other embodiments, a donor label can be present on a first reactant and an acceptor label can be present on a second reactant, where binding of the first reactant and the second reactant bring the labels into such proximity as to permit FRET at a first efficiency, e.g., resulting detectable emissions from both the donor and acceptor label. Further, a third reactant comprising the acceptor label and capable of binding to the first reactant can also be present, where the conformation of the acceptor label on the third reactant is different than the conformation of the acceptor label on the second reactant. As such, binding of the third reactant to the first reactant permits FRET at a second efficiency that is different than the first, and the differing conformations of the second and third reactants and resulting different FRET efficiencies upon binding the first reactant allows identification of the reactant bound based upon the resulting emission spectrum. In yet further embodiments, a donor chromophore may be proximal to but not linked to a first reactant at a reaction site and an acceptor chromophore may be attached to a second reactant that interacts with the first reactant in a manner that brings the donor and acceptor chromophores into close proximity to allow FRET to occur between them at a desired efficiency.

The configuration of a variety of different labeled compounds having the same or similar excitation spectra and multiple different emission spectra has broad utility in a variety of multiplexed analyses, including for example, multi-color nucleic acid sequencing applications, binding assays, enzymatic assays, and protein sequencing applications. In particular, the use of fewer excitation light sources (e.g., a single excitation light source) dramatically reduces engineering constraints for excitation/detection systems, and also provides a more uniform analog structure to potentially provide more predictability and/or uniformity for any biochemistry steps involved in the processes, i.e., except for differences in the base and the acceptor fluorophore.

Labeled Nucleotide Analogs

In certain aspects, the labeled compounds of the invention provide a nucleotide analog comprising a nitrogenous base, a sugar, and a polyphosphate chain, containing phosphorus atoms that are optionally substituted at various side positions, and optionally linked at one or more positions by other than an oxygen atom. Certain embodiments of substituted polyphosphate chains are provided, e.g., in U.S. Pat. No. 7,405,281, which is incorporated by reference herein in its entirety for all purposes. Coupled directly or indirectly to the polyphosphate chain is at least one label that can undergo FRET with at least one other label. In certain preferred embodiments, at least two chromophores that together form a FRET label are coupled to the polyphosphate chain, the conformation of the nucleotide analog (in particular, the distance between the two chromophores in the FRET pair) determinative of the FRET efficiency when exposed to excitation radiation. In certain embodiments, an analytical reaction comprises at least two of such labeled nucleotide analogs, each comprising a different base and each displaying a different FRET efficiency such that the emission spectra upon excitation distinctly identifies the FRET-labeled nucleotide analog, and therefore the base therein. For example, although the same FRET pair may label two different nucleotide analogs, the positioning of the chromophores within the analog can be adjusted to produce a distinguishable emission spectrum for each analog, based at least in part on FRET efficiency. In other embodiments, an analytical reaction comprises at least two of such labeled nucleotide analogs, each comprising a different base and the same type of label that can undergo FRET with another labeled reactant in an analytical reaction, e.g., an enzyme or other protein. For example, although the same label is found on both labeled nucleotide analogs, the conformation (e.g. position, linker structure, and the like) of the label on each analog is different, resulting in a different FRET efficiency upon interaction with the other labeled reactant, and therefore detectably different emission spectra.

In some aspects, the labeled compounds of the invention are analogous to nucleotides. In preferred aspects, the labeled compounds are readily recognized and processed by nucleic acid processing enzymes, such as polymerases. In certain embodiments, the labeled compounds are incorporated into growing polynucleotide strands by polymerase enzymes. In certain aspects, such labeled compounds have incorporation efficiencies that are better than or at least comparable to triphosphate, tetraphosphate, pentaphosphate, or hexaphosphate analogs.

In particular, the labeled nucleotide analogs of the invention are particularly useful as substrates for polymerase enzymes in polynucleotide synthesis and particularly, template-dependent polynucleotide synthesis, e.g., DNA polymerases, i.e., Taq polymerases, E. coli DNA Polymerase I, Klenow fragment, reverse transcriptases, 129 related polymerases including wild type 129 polymerase and derivatives of such polymerases, T7 DNA Polymerase, T5 DNA Polymerase, RNA polymerases, and the like, where such synthesis is a component of a process for the identification of sequence elements in the polynucleotide, e.g., individual bases, contiguous sequences of nucleotides, and/or overall nucleic acid composition, and the like. Another particular advantage of the labeled nucleotide analogs of the invention is that during incorporation into a synthesized nucleic acid strand, the chromophores are cleaved from the nucleotide analog by the action of the polymerase, and thus are not incorporated into the synthesized strand, resulting in the generation of a natural or "native" strand complementary to the template strand. The removal of the chromophores provides a number of benefits including, for example, the avoidance of any steric interference on a subsequent incorporation event. Such steric interference can result from, e.g., bulky or chemically incompatible label groups that can interfere with the action of the synthesis machinery, and can thereby effectively terminate or reduce the rate of continued synthesis. This feature of the methods described herein is beneficial to other kinds of analytical reactions, as well.

It certain specific embodiments, the invention provides a composition comprising a compound of the formula:

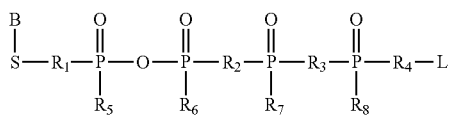

wherein B is a natural or non-natural nucleobase or nucleobase analog; S is selected from a sugar moiety, an acyclic moiety or a carbocyclic moiety; L is a detectable label optionally including a linker; and $R_1$ is selected from O and S. $R_2$, $R_3$ and $R_4$ are independently selected from O, methylene, substituted methylene, ethylene, substituted ethylene, where the substituents may include H, F, Cl, OH, $NH_2$, alkyl, alkenyl, alkynyl, aryl, and heterocycle. In structural terms, the carbons of the substituted methylene or ethylene groups will generally comprise the structure CR'R", where R' and R" are independently selected from H, F, Cl, OH, $NH_2$, alkyl, alkenyl, alkynyl, aryl, and heterocycle. Examples of such groups include, e.g., $CH_2$, $CF_2$, $CCl_2$, $C(OH)(CH_3)$, $C(NH_2)[(CH_2)_6CH_3])$ and $CH_2CH_2$. $R_2$, $R_3$ and $R_4$ are also selected from NH, S, CH(NHR) (where R is H, alkyl, alkenyl, alkynyl, aryl, or heterocycle), C(OH)[$(CH_2)_nNH_2$] (n is 2 or 3), $C(OH)CH_2R$ where R is 4-pyridine or 1-imidazole, and $CNH_2$. In preferred aspects, $R_2$, $R_3$ and in some cases $R_4$, are independently selected from O, NH, S, methylene, substituted methylene, $CNH_2$, $CH_2CH_2$, $C(OH)CH_2R$ where R is 4-pyridine or 1-imidazole.

In addition to the foregoing, $R_4$ is additionally selected from

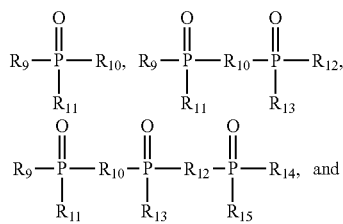

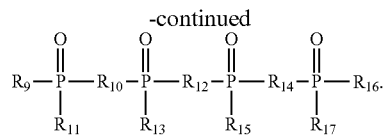

$R_5$, $R_6$, $R_7$, $R_8$, $R_{11}$, $R_{13}$, $R_{15}$ and $R_{17}$ are, when present, each independently selected from OH, $BH_3$, and S; and $R_9$, $R_{10}$, $R_{12}$, $R_{14}$ and $R_{16}$ are independently selected from the same groups as $R_2$ and $R_3$, e.g., O, NH, S, methylene, substituted methylene, $CNH_2$, $CH_2CH_2$, $C(OH)CH_2R$ where R is 4-pyridine or 1-imidazole.

The base moiety ("B") of a labeled nucleotide analogs of the invention is generally selected from any of the natural or non-natural nucleobases or nucleobase analogs, including, e.g., purine or pyrimidine bases that are routinely found in nucleic acids and nucleic acid analogs, including adenine, thymine, guanine, cytidine, uracil, and in some cases, inosine. For purposes of the present description, reference to nucleotide analogs is based upon their relative analogy to naturally occurring nucleotide analogs. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1-N6-ethenoadenosine or pyrrolo-C, in which an additional ring structure renders the base moiety neither a purine nor a pyrimidine. For example, in certain cases, it may be desirable to substitute one or more side groups of the base moiety with a labeling group or a component of a labeling group, such as one of a donor or acceptor chromophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In a labeled nucleotide analog of the invention, the sugar moiety ("S"), in its most preferred aspect, is selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties may be substituted for a sugar moiety, including, e.g., those described in published U.S. Patent Application No. 2003/0124576, previously incorporated herein by reference in its entirety for all purposes.

For most cases, the polyphosphate chain in the compounds of the present invention, e.g., a triphosphate in conventional NTPs, is preferably coupled to the 5' hydroxyl group, as in natural nucleoside triphosphates. However, in some cases, it may be desirable that the polyphosphate chain is linked to the sugar moiety by the 3' hydroxyl group. In certain embodiments, the polyphosphate chain comprises at least about 3, 4, 5, 6, 7, or 8 phosphates. In certain preferred embodiments, the polyphosphate chain comprises about 4-7 phosphates, with specific embodiments comprising 6 phosphates. Further, while the compounds of the invention are generally described in terms of including four or more phosphorus groups in the phosphorus containing chain, it will be appreciated that in some instances a three phosphorus atom containing chain may be desired.

In certain aspects, the elongated polyphosphate chain, e.g., containing four or more phosphorus atoms in a linear configuration, is believed to provide an advantage in the presently described compounds by placing labeling molecules that may be foreign to nucleotide processing enzymes, e.g., DNA polymerases, away from the relevant portion of the analog and/or away from the active site of the enzyme. Such spacing is believed to reduce the potential for photo-induced damage, e.g., as described further in U.S. Ser. No. 61/116,048, filed Nov. 19, 2008; US Pat. Pub. No. 20070128133, filed Dec. 12, 2005; US Pat. Pub. No. 20070161017, filed Dec. 1, 2006; and US Pat. Pub. No. 20080176241, filed Oct. 31, 2007. In addition to providing such distance through the polyphosphate chain, additional linker molecules may be used to provide additional distance between the nucleoside portion of the analog and the label groups. In particular, while one of the label groups may be directly coupled to the terminal phosphorus atom of the analog structure, in alternative aspects, it may additionally include a linker molecule to provide an indirect coupling to the terminal phosphorus atom through, e.g., an alkylphosphonate linkage.

In addition to substitution at the inter-phosphorus linkages, the compounds of the invention are also optionally substituted at one or more of the side groups of the phosphorus atoms (or alpha phosphate). Typically, substitution at these side groups, and particularly those more distal than the alpha phosphate, will have little negative impact on the incorporation of the analog into a growing nucleic acid strand by a nucleic acid polymerase. In some cases, incorporation of certain groups at such side groups is expected to provide improved efficiency of incorporation or processivity of the polymerase enzymes. In particular, boronation of one or more of the subject side groups is expected to provide such enhanced incorporation. In particularly preferred aspects, the at least one of the oxygen groups on the α phosphate are substituted with Boron, and more preferably, the boronated-α-phosphate is the Rp stereo isomer (See, Ramsey-Shaw, et al., Reading, Writing and Modulating Genetic Information with Boranophosphate Mimics of Nucleotides, DNA, and RNA, (2003) Ann. N.Y. Acad. Sci. 1002:12-29, which is incorporated herein by reference in its entirety for all purposes). Such α-P-Borane substitutions have been shown to improve substrate characteristics for nucleotide analogs, i.e., AZT triphosphate, d4T triphosphate, and 3TCTP in reactions with HIV-1 RT (See, Phillippe Meyer et al., EMBO J. (2000) 19:3520-3529, and Jerome Deval, et al., J. Biol. Chem. (2005) 280:3838-3846). Additionally, borane modified nucleic acids have been shown to be resistant to exonucleoase activity (See Ramsey-Shaw et al. supra.). In accordance with certain preferred uses of the compounds of the invention, increased stability of a nascent nucleic acid strand to exonuclease activity can be of substantial value, in preventing auto-corrections for misincorporation of a nucleotide during the synthesis process. Such corrections can yield substantial data analysis problems in processes that utilize real time observation of incorporation events as a method of identifying sequence information.

In certain aspects of the invention, the label portion ("L") of a compound comprises at least one detectable moiety, and in certain preferred embodiments at least two detectable labeling moieties, and at least one or more linking groups. In certain preferred embodiments, at least one of the detectable labeling moieties is indirectly coupled to a phosphorus atom in a polyphosphate chain (e.g., the terminal phosphorus atom) via at least one linking group. In some embodiments, at least one of the detectable labeling moieties is directly coupled to a phosphorus atom in a polyphosphate chain. In some embodiments, at least two detectable labeling moieties are indirectly coupled to one or more phosphorus atoms in a polyphosphate chain via at least one linking group. In certain preferred embodiments, the detectable labeling moieties in a compound of the invention form at least one Förster resonant energy transfer ("FRET") pair. For example, the FRET pair may be formed within a single labeled compound (intramolecular FRET) or may be formed between multiple labeled compounds (intermolecular FRET). As used herein, intermolecular FRET includes not only FRET between labels on reactants, but also FRET between a labeled reactant and a label on a non-reactant entity or surface in a reaction, e.g., at a reaction site, on a linker, or on a bead, solid surface, or other substrate upon which the reaction is localized.

Detectable labeling moieties, and in particular those that can form a FRET pair, are described at length herein. As noted above, the labeling moieties can comprise optically detectable moieties, including luminescent, chemiluminescent, fluorescent, fluorogenic, chromophoric and/or chromogenic moieties, with fluorescent and/or fluorogenic labels being particularly preferred. For example, a variety of different label moieties are readily employed in nucleotide analogs, and particularly, the compound of the invention. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen/Life Technologies, Inc., and described in 'The Handbook—A Guide to Fluorescent Probes and Labeling Technologies, Tenth Edition' (2005) (available from Invitrogen, Inc./Molecular Probes/Life Technologies), semiconductor nanocrystals and other nanoparticle labels (e.g., Qdot® nanocrystals available from Invitrogen, Inc. (Life Technologies)). A variety of other labeling moieties for use with labeled compounds (e.g., nucleoside polyphosphates and other biomolecules and reaction components), and which would be applicable to the compounds of the present invention are described in, e.g., Published U.S. Patent Application No. 2003/0124576, the full disclosure of which is incorporated herein in its entirety for all purposes. Additional examples of useful FRET labels include, e.g., those described in U.S. Pat. Nos. 5,654,419, 5,688,648, 5,853,992, 5,863,727, 5,945,526, 6,008,373, 6,150,107, 6,335,440, 6,348, 596, 6,479,303, 6,545,164, 6,849,745 and 6,696,255, and Published U.S. Patent Application No. 2003/0143594, the disclosures of which are incorporated herein by reference for all purposes. In certain preferred embodiments, the chromophores in a FRET pair are fluorophores.

For a number of applications, it may be desirable to utilize a different type of label portion for each different labeled compound, e.g., each nucleotide analog that includes a different base, e.g., A, T, G, C, U, I, or analogs or derivatives thereof. In such cases, the label portions may be selected so that each label portion has an emission spectrum that is distinguishable from the emission spectrum of other label portions. Such distinguishable labeled nucleotide analogs provide an ability to monitor the presence of different labeled compounds simultaneously in the same reaction mixture. In applications in which multiple different label portions are used to label different compounds, label portions may be selected to include overlapping excitation spectra, so as to avoid the necessity for multiple different excitation sources, while providing clearly distinguishable emission spectra.

In certain preferred embodiments, multicomponent label portions are employed to differentially label at least one or more different reaction components, e.g., different nucleotide analogs. For example, as noted above, FRET labels may be used in the compounds of the invention. FRET labels are discussed at length above. In preferred embodiments, the molecular structure of a FRET-labeled compound may comprise one or more linkers that function to distance the chromophores from the reactive portion and/or to specifically position the chromophores with respect to one another, e.g., for controlling intramolecular or intermolecular FRET efficiency under excitation illumination.

Figure 2:
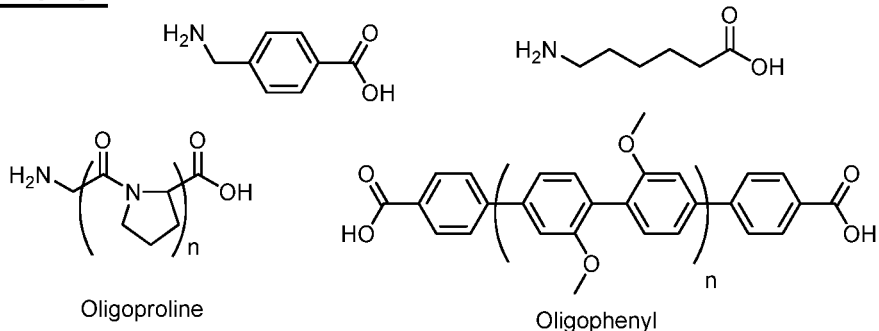
FIG. 2 illustrates various different linker components for the construction of FRET labels as described herein.
Figure 2:
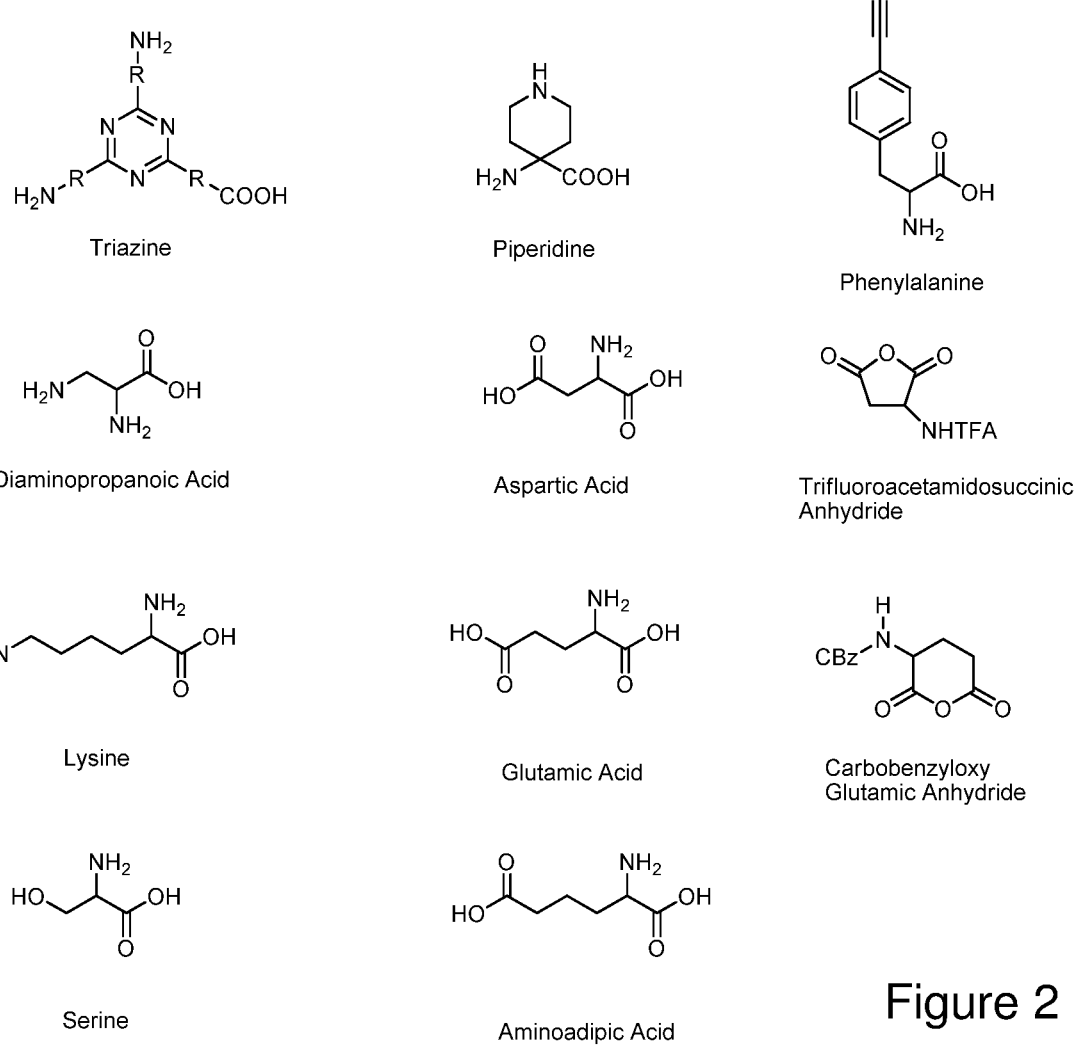

In some embodiments of the labeled compounds provided herein, a single linker comprises a single chromophore in a FRET label, in other embodiments a single linker comprises multiple chromophores in a FRET label, and in yet further embodiments, multiple linkers, each comprising one or more chromophores in a FRET label, are attached to a single labeled component. For example, in a labeled nucleotide analog, one or multiple linkers may be attached to the polyphosphate chain, each comprising at least one chromophore. Such multiple linkers may be bound to the same or different phosphates in the polyphosphate chain. In some embodiments, the configuration of a labeled nucleotide analog is dependent upon which phosphate is linked to the chromophore. For example, in certain embodiments a plurality of nucleotide analogs are distinguished from one another based upon the position of an acceptor chromophore relative to the polyphosphate chain. By positioning the acceptor chromophore at different locations on the polyphosphate chain, the distance to the donor chromophore, and therefore FRET efficiency, can be adjusted. As noted elsewhere herein, the donor and acceptor may be carried on the same analog, or the donor may be linked to the reaction site or another component with which the nucleotide analog is expected to interact, e.g., an enzyme such as a polymerase, nuclease, phosphatase, and the like. Linkers of the invention that comprise phosphorus atoms may differ from polyphosphates by virtue of the inclusion of one or more phosphonate groups, effectively substituting a non-ester linkage in the phosphorous containing chain of the nucleotide analog, with a more stable linkage. Examples of linking groups include, e.g., $CH_2$, methylene derivatives (e.g., substituted independently at one or more hydrogens with F, Cl, OH, $NH_2$, alkyl, alkenyl, alkynyl, etc.), $CCl_2$, $CF_2$, NH, S, $CH_2CH_2$, C(OH)$(CH_3)$, $C(NH_2)[(CH_2)_6CH_3]$, CH(NHR) (R is H or alkyl, alkenyl, alkynyl, aryl, $C(OH)[(CH_2)_nNH_2]$ (n is 2 or 3), and $CNH_2$. In particularly preferred aspects, methylene, amide or their derivatives are used as the linkages. Linking groups may be linear, tridentate, or polydentate, and certain preferred but nonlimiting examples of both linear and tridentate linking groups are provided in FIG. 2.

In preferred aspects, the compounds include one, two or three such linkages, but retain an alpha phosphate that is coupled to the sugar (or carbocyclic or acyclic) moiety of the nucleotide analog. Retention of the alpha phosphate group yields several benefits in the compounds of the invention. In particularly preferred embodiments, it permits cleavage of the beta and more distal phosphorus groups and the associated label from the nucleotide analog by a polymerase enzyme during processing by that enzyme. Additionally, once processed, the nucleotide analog is more closely analogous (and in some embodiments, identical) to a naturally occurring, processed nucleotide, allowing base dependent hybridization and further minimizing any steric or other enzyme related effects of incorporation of a highly heterologous compound into a growing nucleic acid strand.

Examples of certain preferred compounds of the invention include those shown below:

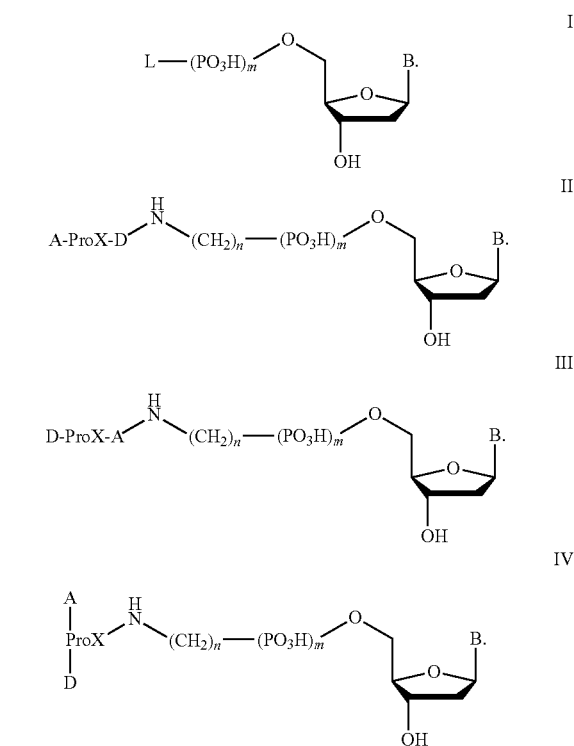

The base moiety ("B") is as described above. The sugar moiety is a deoxyribose sugar. A polyphosphate chain contains m phosphates, where m is an integer from three to eight. Three variations of the label portion ("L") in structure I are shown in the structures II, III, and IV, and all of these comprise an unbranched alkyl group, an amine, and a polyproline chain of length X ("ProX") that is bound to both the acceptor chromophore ("A") and the donor chromophore ("D"). In certain preferred embodiments, X is an integer of at least about 5 to 40, more preferably 5 to 20, and its length in any particular compound dependent upon various experimental considerations, for example, the desired FRET efficiency and the characteristics and positions of the chromophores bound thereto. In some embodiments, a polyproline chain of 6 to 14 proline residues provides a preferred separation or distance between chromophores in a FRET label. Either the donor or acceptor chromophore may attached to the polyproline chain at a position proximal to the nucleobase portion of the compound, as shown in the structures II and III, respectively. Further, the polyproline chain may be attached directly to the amine group, with the donor and acceptor chromophores attached at positions along its length that promote a desired FRET efficiency, as shown in structure IV. In some preferred embodiments, the acceptor and donor chromophores are linked to the polyproline chain by amino- and carboxyl-terminal glycine and cysteine residues, respectively, and vice versa, by chemical methods known to those of ordinary skill in the art. See, e.g., Schuler, B. (2005) Proc. Natl. Acad. Sci. 102(8):2754-2759, incorporated by reference herein in its entirety for all purposes. Further, although unbranched alkyl groups are shown in these exemplary embodiments, substituted alkyl groups may also be used in such linker structures, as described herein.

Although shown for purposes of illustration, it will be appreciated that the compounds of the invention encompass a range of variability, including, in particularly preferred aspects, that which is set forth in the appended claims.

II. Analytical Reactions

The compounds and compositions of the invention have a variety of different uses and applications, including use in performing analytical reactions. The labeled compounds of the invention are particularly useful in analytical reactions in which multiple components of a reaction mixture must be differentially labeled. The labeled compounds of the invention are also particularly useful in analytical reactions in which the number of preferred labeling moieties is limited by exclusion of labeling moieties that negatively impact the analytical reaction.

In certain aspects, the labeled compounds of the invention are particularly useful in performing nucleic acid analyses. For example, such compounds may be used to detect association of nucleotide analogs with other reaction components, e.g., resulting in incorporation of the nucleotide analogs into a growing nucleic acid (e.g., DNA or RNA) strand. While preferred embodiments of the invention relate to nucleic acid molecules, including nucleotide analogs, oligonucleotides, and polynucleotides that include the foregoing features, the principles of the invention are equally applicable to a broad range of reactants, labeling groups, and/or enzyme systems, including, e.g., kinases, phosphatases, ribosomes, receptors, helicases, ligands, nucleases, phosphatases, kinases, ligases, substrates, complexes, binding partners, etc. For ease of discussion however, the invention is described in terms of chromophore-labeled nucleotide analogs and their interaction with nucleic acid processing enzymes, including DNA and RNA polymerases, reverse transcriptases, nucleases, ligases, helicases, and the like, with DNA and RNA polymerases being particularly preferred enzyme systems. In addition to their use in sequencing, the analogs of the invention are also equally useful in a variety of other genotyping analyses, e.g., SNP genotyping that uses single-base extension methods, real-time monitoring of amplification, RT-PCR methods, and the like.

In particularly preferred embodiments, the labeled compounds of the invention comprise chromophore-labeled nucleotide analogs used in enzymatic reactions, particularly real-time analytical reactions where one observes chemical reactions through the detection of an emission of light. For example, labeled nucleotide analogs are particularly useful in polymerization reactions in which the label is excited during the synthesis process by exposure to excitation illumination. One particularly important example of such a reaction includes polymerase-mediated, template-dependent synthesis of nucleic acids that can be observed using real-time techniques for a variety of desired goals, including in particular determination of information about the template sequence. A number of methods have been proposed for determination of sequence information using incorporation of fluorescent or fluorogenic nucleotides into the synthesized strand by a DNA or other polymerase, and the compositions and methods of the invention are applicable to these methods. While several of these methods employ iterative steps of nucleotide introduction, washing, optical interrogation, and label removal, certain preferred uses of these compositions utilize "real-time" determination of incorporation, in particular during processive incorporation of nucleotides into a nascent strand. Such methods are described in detail in, for example, U.S. Pat. Nos. 7,056,661, 7,052,847, 7,033, 764 and 7,056,676, the full disclosures of which are incorporated herein by reference in their entirety for all purposes.

In certain embodiments, a reaction of interest, e.g., a polymerase reaction, can be isolated within an extremely small observation volume that effectively results in observation of individual molecules, for example, by using optical techniques that illuminate small volumes around the complex with excitation radiation, e.g., total internal reflection microscopy (TIRF) methods, waveguide arrays, optical confinements like nanoholes and Zero Mode Waveguides (ZMWs), and the like, and combinations thereof. In preferred embodiments, such methods provide optical resolvability between individual reaction sites and allow observation of a single reaction without interference from other reactions occurring in the reaction mixture. For example, one can identify individual nucleobase incorporation events based upon the optical signature of the label portion of a labeled nucleotide analog as compared to non-incorporated, randomly diffusing labeled nucleotide analogs; or individual ligands binding to a receptor of interest; or individual amino acids incorporated into a nascent polypeptide strand. In a preferred aspect, such small observation volumes are provided by immobilizing the polymerase enzyme within an optical confinement, such as a Zero Mode Waveguide (ZMW). For a description of ZMWs and other means of reducing observation volumes and providing optical resolvability for monitoring individual molecules, enzymes, complexes, and the like, and their application in single molecule analyses, and particularly nucleic acid sequencing, see, e.g., U.S. Ser. No. 12/560,308, filed Sep. 15, 2009; Published U.S. Patent Application Nos. 2003/0044781, 2008/0128627, 2008/0152281, and 2008/01552280; and U.S. Pat. Nos. 6,917,726, 7,013,054, 7,181,122, 7,292,742, 7,170,050, and 7,302,146, each of which is incorporated herein by reference in its entirety for all purposes.

In accordance with one aspect of the methods of invention, the compounds described herein are used in analyzing nucleic acid sequences using a template-dependent sequencing reaction to monitor the template-dependent incorporation of specific nucleotide analogs into a synthesized nucleic acid strand, and thereby determine a sequence of nucleotides present in a template nucleic acid strand. In certain specific embodiments, a template-dependent sequencing reaction comprises providing a template nucleic acid (e.g., DNA or RNA) complexed with a polymerase enzyme in a template-dependent polymerization reaction, contacting the polymerase and template nucleic acid with a labeled nucleotide analog of the invention, detecting whether or not the labeled nucleotide analog is incorporated into a nascent nucleic acid strand during the polymerization reaction, and identifying a base in the template strand based upon incorporation of the labeled nucleotide analog. Such analytical reactions systems can comprise intramolecular FRET labels, intermolecular FRET labels (e.g., where one label is on or proximal to the polymerase and the other label is on the nucleotide), non-FRET labels, or a combination thereof. When a particular base in the template strand is encountered by the polymerase during the polymerization reaction, it complexes with an available nucleotide analog that is complementary to the template nucleotide, and that analog is incorporated into the nascent and growing nucleic acid strand, e.g., by cleaving between the α and β phosphorus atoms in the analog, and consequently releasing the labeling group (or a portion thereof). The incorporation event is detected, either by virtue of a longer presence of the labeled analog in the complex, or by virtue of release of the label group into the surrounding medium. By providing each different type of nucleotide analog with a distinguishable label, e.g., having a distinguishable emission spectrum, identification of the label of an incorporated analog allows identification of that analog, and consequently the complementary sequence of the template can be deduced based on the sequence of nucleotides incorporated into the nascent strand. For example, different nucleotide analogs may comprise the same FRET labeling moieties in different conformations, or different FRET labels altogether, or non-FRET labels, or different acceptor labels that emit different emission spectra in the presence of the same donor label, e.g., on the polymerase or at the reaction site, or a combination thereof. For example, by changing the location of an acceptor group on the nucleotide analog, the distance from a donor group, e.g., on the polymerase, and the resulting emission spectrum is changed. Alternatively or additionally, the location of the donor group can also be adjusted to change the FRET efficiency of the FRET label. In some embodiments, all labeled nucleotide analogs in the reaction comprise a FRET label; in other embodiments, some of the labeled nucleotide analogs in the reaction comprise a FRET label and other labeled nucleotide analogs in the reaction comprise a non-FRET label. In preferred aspects, labeled compounds of the invention present in the reaction are compounds analogous to at least one of the four natural nucleotides, A, T, G and C. In preferred embodiments, incorporation of labeled nucleotide analogs is detected in real-time during nascent strand synthesis. Preferably, the foregoing process is carried out so as to permit detection/identification of individual nucleotide incorporation events, through the use of, for example, an optical confinement that allows observation of an individual polymerase enzyme, or through the use of a heterogeneous assay system, where label groups released from incorporated analogs are detected. In particularly preferred aspects, the polymerase enzyme/template complex is provided immobilized within an optical confinement that permits observation of an individual complex, e.g., a zero mode waveguide.

In accordance with one aspect of the methods of invention, the compounds described herein are used in analyzing polypeptide sequences using an mRNA translation reaction to monitor and determine the incorporation of amino acids into a synthesized polypeptide chain. In certain specific embodiments, a translation reaction comprises providing a template mRNA complexed with a ribosome, contacting the ribosome and template mRNA with a labeled tRNA analog, detecting whether or not the amino acid carried by the labeled tRNA analog is incorporated into a nascent polypeptide chain, and identifying an amino acid so incorporated, e.g., based upon the label carried by the tRNA analog. For example, the incorporation event can be detected by virtue of a longer presence of the labeled tRNA analog in the complex. By providing each different type of tRNA analog with a distinguishable label, e.g., having a distinguishable emission spectrum, identification of the label of a tRNA analog that associates with the ribosome allows identification of the analog and the amino acid it carries. Such analytical reactions systems can comprise intramolecular FRET labels, intermolecular FRET labels (e.g., where one label is on or proximal to the ribosome and the other label is on the tRNA), non-FRET labels, or a combination thereof. For example, different tRNA analogs may comprise the same FRET labeling moieties in different conformations, or different FRET labels altogether, or non-FRET labels, or different acceptor labels that emit different emission spectra in the presence of the same donor label, e.g., on the ribosome or at the reaction site, or a combination thereof. For example, by changing the location of an acceptor group on the tRNA analog, the distance from a donor group, e.g., on the ribosome, and the resulting emission spectrum is changed. Alternatively or additionally, the location of the donor group can also be adjusted to change the FRET efficiency of the FRET label. Various labeling strategies for and other aspects of translation-based protein sequencing are provided in U.S. Ser. No. 61/186,645, filed Jun. 12, 2009, the disclosure of which is incorporated herein by reference in its entirety for all purposes. In some embodiments, all labeled tRNA analogs in the reaction comprise a FRET label; in other embodiments, some of the labeled tRNA analogs in the reaction comprise a FRET label and other labeled tRNA analogs in the reaction comprise a non-FRET label. In preferred embodiments, incorporation of amino acids is detected in real-time during translation. Preferably, the foregoing process is carried out so as to permit detection/identification of individual amino acid incorporation events, through the use of, for example, an optical confinement that allows observation of an individual ribosome. In particularly preferred aspects, the ribosome/mRNA complex is provided immobilized within an optical confinement that permits observation of an individual complex, e.g., a zero mode waveguide.

As noted above, in a typical template-dependent synthesis reaction, each nucleotide to be incorporated bears a label that identifies the nitrogenous base portion of the nucleotide, so in typical nucleic acid synthesis reactions four such labels are present to differentially label the four different nucleotides (e.g., A, C, G, and T). Detection of multiple chromophores in a single analytical reaction introduces challenges related not only to excitation and detection, but also the variations in performance and the potential for negative effects associated with the use of certain chromophores (e.g., photodamage). In certain aspects, the compounds, methods, and compositions provided herein are particularly useful for reducing the number of chromophores needed to differentially label multiple components of an analytical reaction. In certain embodiments, this is accomplished by using a single combination of FRET label moieties to label multiple reaction components ("labeled compounds"), and varying the structure of the labeled compounds such that different reactive portions (e.g., nucleotide analogs) are linked to FRET labels having different orientations and therefore producing different and distinct emission spectra. In certain aspects, a single combination of FRET label moieties may be used to provide at least about 2-10 different emission spectra based on the orientation of the chromophores relative to one another, and can be used to label compounds including not only nucleotide analogs, but also other types of reactants described herein and elsewhere, including enzymes, tRNAs, binding partners, ligands, receptors, cofactors, and the like. Further, as described elsewhere herein, such FRET labels can be intramolecular FRET labels or intermolecular FRET labels, e.g., in which a donor chromophore is attached to one labeled compound and an acceptor chromophore is attached to a second labeled compound. In certain embodiments, multiple different reactants carry the same acceptor chromophore, and the configuration of the acceptor chromophore on each reactant is designed to produce a distinct and recognizable emission spectrum that can be used to distinguish between the different reactants when they undergo FRET with the donor chromophore.

In certain embodiments, FRET-labeled compounds may be combined with non-FRET-labeled compounds in a single analytical reaction. For example, a single reaction may include at least one or two of the nucleotide analogs that comprise a FRET label and at least one or two nucleotide analogs that do not comprise a FRET label, with identification of the incorporated nucleotide analog based at least in part on a comparison of the emission spectra generated during polymerization of the nascent strand. In preferred embodiments, incorporation of labeled nucleotide analogs, whether FRET-labeled or non-FRET-labeled (i.e., comprising a detectable label that does not undergo FRET), is detected in real-time during nascent strand synthesis. In a specific embodiment of a polymerase-mediated, template-directed synthesis reaction, two chromophores may be used to distinctly label the four nucleotide analogs to be incorporated into the nascent strand. For example, a first nucleotide analog is labeled with chromophore A, a second nucleotide analog is labeled with chromophore B, a third nucleotide analog is labeled with the A-B FRET pair in a first orientation, and a fourth nucleotide analog is labeled with the A-B FRET pair in a second orientation. In this way, four different emission spectra are produced in a single analytical reaction using only two chromophores, two of the emission spectra being produced from FRET pairs having different conformations and therefore different FRET efficiencies. Although this prophetic example describes a reaction comprising two FRET-labeled compounds that comprise the same two chromophores, the present invention also contemplates reactions in which multiple FRET-labeled compounds in a single reaction may share more or fewer than two chromophores. Further, as noted above, reactions utilizing the labeled compounds of the invention may comprise a combination of FRET and non-FRET labeled compounds, may comprise intramolecular and/or intermolecular FRET labels, and may comprise labeled compounds having multiple labeling moieties that do not undergo FRET.

In various embodiments of the methods provided herein, one or more components of an analytical reaction are immobilized. Such immobilization can be engineered in various ways using methods well known to the ordinary practitioner and routinely practiced in the art. For example, immobilization of enzymes or other proteins may employ any of a variety of techniques, including, for example, in vivo biotinylation of a N- or C-terminal peptide tag on the protein (e.g. AviTag (Avidity)) (see, e.g., D. Beckett, et al., *Protein Sci* 1999, 8, 921, which is incorporated herein by reference in its entirety for all purposes), which provides high efficiency of biotinylation and preservation of enzymatic activities or other characteristics, such as binding specificity, higher order structure, etc. A variety of other surface treatments are also optionally exploited to avoid non-specific interactions of free reagents and the surfaces of the illumination volume, which could give rise to aberrant signals. For example, polyphosphonate and silane-based surface coatings may be exploited that mediate enzyme attachment to the transparent floor of a zero mode waveguide while blocking non-specific attachments to the metal top and side wall surfaces (see, e.g., J. Eid, et al. (incorporated herein above) and J. Korlach, et al., *Proc Natl Acad Sci USA* 2008, 105, 1176, which is incorporated herein by reference in its entirety for all purposes).

One skilled in the art will appreciate that there are many ways of immobilizing nucleic acids and proteins into an optical confinement, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others.

In some embodiments, antibodies specific for one or more reaction components are used to bind and immobilize the reaction components to reaction sites, e.g., particular locations on a substrate, in a way that maintains their ability to participate in an analytical reaction of interest. This method of immobilization is especially useful where the reactants are being collected from a sample to be applied to the reaction site. Further, nucleic acid molecules may be directly linked to a reaction site, or may be indirectly linked, e.g., through interaction with a primer or other moiety directly linked to the reaction site. Such a primer may be designed to be complementary to a particular region or multiple regions of interest in the RNA template(s), may be randomly generated, or may be an olito(dT) that will anneal to the poly-dA tail on mRNAs. In addition, a silyl moiety can be attached to a nucleic acid directly to a substrate such as glass using methods known in the art. In certain embodiments, a biomolecular complex is assembled in at a reaction site, e.g., by first immobilizing an enzyme component. In other embodiments, such a complex is assembled in solution prior to immobilization. Various additional methods for immobilizing molecular complexes are provided, e.g., in U.S. Pat. No. 7,476,503, which is incorporated herein by reference in its entirety for all purposes. In preferred embodiments, reaction components are immobilized at a reaction site such that signals emitted from each resulting analytical reaction are optically resolvable from signals emitted from every other analytical reaction at every other reaction site, e.g., on a substrate. Immobilized reaction component may or may not comprise a detectable label, e.g., one or more chromophores of a FRET label.

Where desired, an enzyme or other protein reaction component to be immobilized may be modified to contain one or more epitopes such as Myc, HA (derived from influenza virus hemagglutinin), poly-histadines, and/or FLAG, for which specific antibodies are available commercially. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of an optical confinement of the present invention.

The binding moieties or agents of the reaction components they immobilize can be applied to a reaction site by conventional chemical techniques which are well known in the art. In general, these procedures can involve standard chemical surface modifications of a support, incubation of the support at different temperature levels in different media comprising the binding moieties or agents, and possible subsequent steps of washing and cleaning. Further, various means of loading multiple biological reactions onto a substrate are known to those of ordinary skill in the art and are described further, e.g., in U.S. Ser. No. 61/072,641, incorporated herein by reference in its entirety for all purposes.

III. Systems

The present invention also employs the nucleotide analog compounds and compositions described herein in conjunction with overall analytical systems. Typically, such systems employ a reaction region or reaction site that is typically disposed in a reaction vessel or well. By way of example, such systems may include a substrate component upon which are immobilized, e.g., a polymerase/template/primer complex, for use in the determination of nucleic acid sequence information of the template, which may be derived from an organism of interest.

Figure 6:
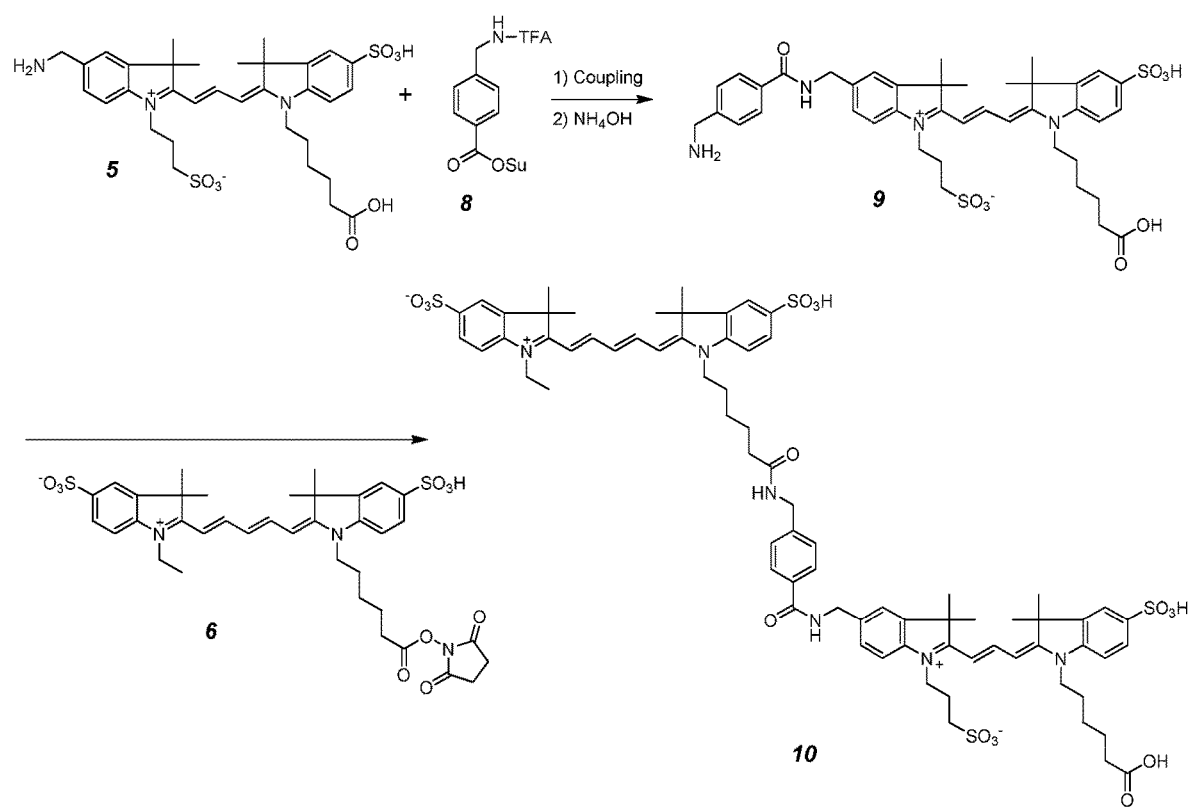
FIG. 6 provides a synthesis scheme for the Cy5-amb-Cy3 compound depicted in FIG. 4.

Because the compositions of the invention are preferably chromophore-labeled, it will be appreciated that the preferred systems of the invention will comprise chromophore emission detection functionalities. Examples of such systems include those described in, e.g., Published U.S. Patent Application Nos. 2007/0036511 and 2007/095119 and U.S. patent application Ser. No. 11/901,273 filed Sep. 14, 2007, the full disclosures of which are incorporated herein by reference in their entirety for all purposes. One such system is schematically illustrated in FIG. 6.

Figure 3:
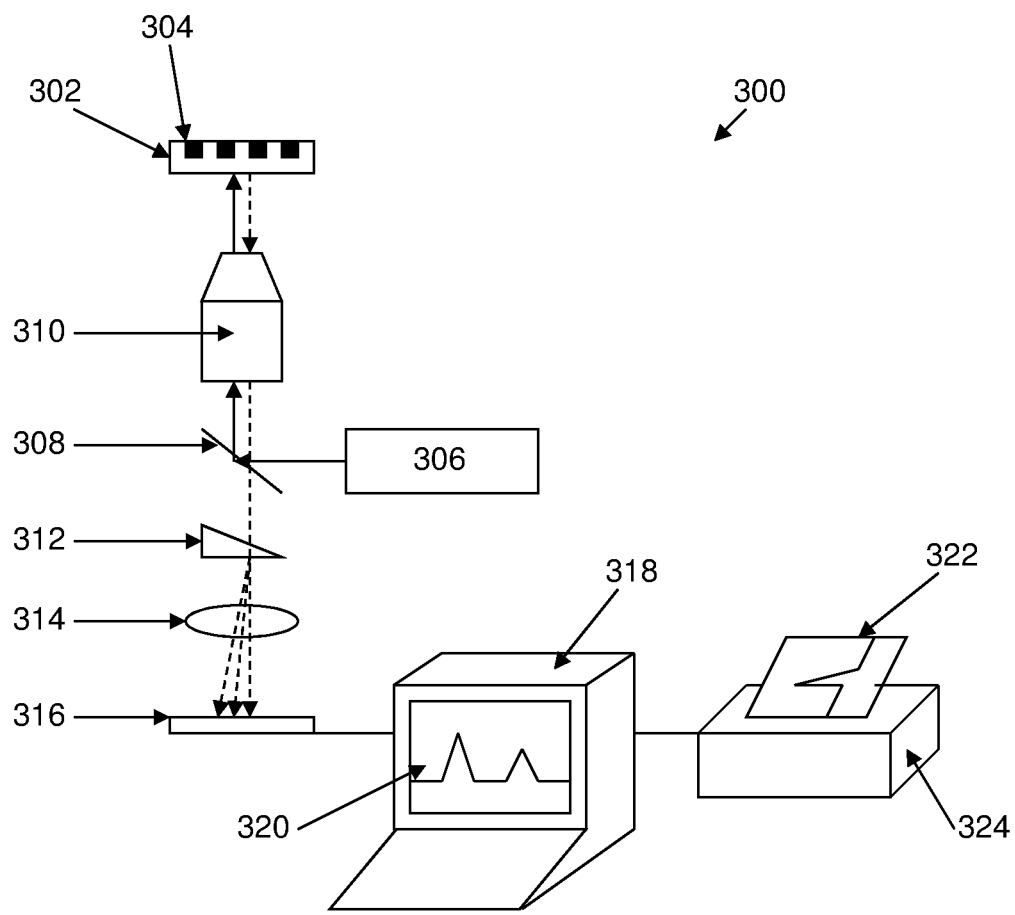
FIG. 3 schematically illustrates one embodiment of a system for use with the compounds and compositions in the methods of the invention.

As shown in FIG. 3, the system 300 includes a substrate 302 that includes a plurality of discrete sources of chromophore emission signals, e.g., an array of zero mode waveguides 304. An excitation illumination source, e.g., laser 306, is provided in the system and is positioned to direct excitation radiation at the various signal sources. This is typically done by directing excitation radiation at or through appropriate optical components, e.g., dichroic 108 and objective lens 310, that direct the excitation radiation at the substrate 302, and particularly the signal sources 304. Emitted signals from the sources 304 are then collected by the optical components, e.g., objective 310, and passed through additional optical elements, e.g., dichroic 308, prism 312 and lens 314, until they are directed to and impinge upon an optical detection system, e.g., detector array 316. The signals are then detected by detector array 316, and the data from that detection is transmitted to an appropriate data processing unit, e.g., computer 318, where the data is subjected to interpretation, analysis, and ultimately presented in a user ready format, e.g., on display 320, or printout 322, from printer 324. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901,273, all of which are incorporated herein by reference in their entireties for all purposes).

In certain aspects, the methods provide a means for studying analytical reactions in vitro by immobilizing at least one component of a analytical reaction in an optical confinement, labeling at least one other component, and detecting signals from the optical confinement during the reaction in real time. An optical confinement is preferentially configured to provide tight optical confinement so only a small volume of the reaction mixture is observable, i.e., signals can only be detected from a small volume of the reaction mixture. In certain embodiments, optical confinement technologies include zero mode waveguides, total internal reflection microscopy (TIRF), and/or optical waveguides (planar or otherwise configured). For example, in embodiments in which excitation illumination is used to excite chromophore-containing labels, the tight optical confinement allows only a small volume of the reaction mixture to be illuminated, and therefore limits excitation to only those chromophores within that small volume. As such, only the chromophores present in the small illuminated volume are excited and emit signals that are detectable by the optical system. This feature of the invention is useful for reducing the background signal from freely diffusing detectably labeled components in the reaction mixture, thereby enabling the use of physiological concentrations of these reagents. Some such optical confinements and methods of manufacture and use thereof are described at length in, e.g., U.S. Pat. Nos. 7,302,146, 7,476,503, 7,313,308, 7,315,019, 7,170,050, 6,917,726, 7,013,054, 7,181,122, and 7,292,742; U.S. Patent Publication Nos. 20080128627, 20080152281, and 200801552280; and U.S. Ser. No. 11/981,740, all of which are incorporated herein by reference in their entireties for all purposes. The optical confinements can be further tailored in various ways for optimal confinement of an analytical reaction of interest. In particular, the size, shape, and composition of the optical confinement can be specifically designed for containment of a given enzyme complex and for the particular label and illumination scheme used.

Providing such individually resolvable configurations can be accomplished through a number of mechanisms, and typically involves immobilization of at least one component of an analytical reaction at a reaction site. For example, by providing a dilute solution of complexes on a substrate surface suited for immobilization, one will be able to provide individually optically resolvable complexes. (See, e.g., European Patent No.1105529 to Balasubramanian, et al., the full disclosure of which is incorporated herein by reference in its entirety for all purposes.) Alternatively, one may provide a low density activated surface to which complexes are coupled. (See, e.g., Published International Patent Application No. WO 2007/041394, the full disclosure of which is incorporated herein by reference in its entirety for all purposes). Such individual complexes may be provided on planar substrates or otherwise incorporated into other structures, e.g., zero mode waveguides or waveguide arrays, to facilitate their observation. In preferred embodiments, a substrate comprises at least one optical confinement in which a molecule or molecular complex is immobilized and monitored. The optical confinement is a structure configured to isolate the immobilized molecule/complex from any other molecule/complex immobilized on the substrate, and in particular to isolate any detectable signals emitted from the optical confinement from any other signals emitted from any other optical confinements on the substrate. Such isolation allows the practitioner of the instant invention to unambiguously assign a detected signal to a single optical confinement on the substrate, and therefore to a single analytical reaction on the substrate.

IV. Kits

The present invention also provides kits useful for exploiting the compounds and compositions described herein in a number of applications. In a first respect, such kits typically include one or more labeled compounds (e.g., labeled compounds that undergo intramolecular or intermolecular FRET, e.g., FRET-labeled nucleotide analogs) of the invention packaged in a fashion to enable their use, and preferably a composition comprising a set of differentially labeled compounds. In certain embodiments, a subset of the set of differentially labeled compounds comprise FRET labels and a subset of the differentially labeled compounds comprise non-FRET labels, e.g., comprising a single or multiple labeling moieties. In certain embodiments, a kit comprises at least four different nucleotide analogs, namely those that are analogous to A, T, G, and C, where each bears a detectably different labeling group to permit its individual identification in the presence of the others. In other embodiments, a kit comprises different tRNA analogs that are analogous to natural tRNA molecules, at least some of which bear detectably distinct labeling groups to permit their individual identification in polypeptide synthesis reactions. Other kits comprise labeled components for other types of analytical reactions, including antibody assays, hybridization assays, genotyping assays, enzymatic assays, binding assays, etc. Depending upon the desired application, the kits of the invention optionally include additional reagents which may or may not comprise labels, such as enzymes for performing analytical reactions employing the labeled compounds of the invention, and other reagents, such as buffer solutions and/or salt solutions, including, e.g., divalent metal ions, i.e., $Mg^{++}$, $Mn^{++}$ and/or $Fe^{++}$, cofactors, standard solutions, e.g., dye standards for detector calibration. In some preferred embodiments, a kit of the invention includes polymerase enzymes for performing template-dependent synthesis employing the labeled nucleotide analogs of the invention, ribosomes for performing protein synthesis reactions, transcription factors for performing nucleic acid binding assays, etc. Each of the different types of labeled compounds in a kit will typically comprise a distinguishable labeling group, as set forth above. Examples of polymerases that are preferably included in a kit of the invention include, e.g., phi29 derived polymerases and the polymerase enzymes described in, e.g., Published International Patent Application Nos. WO 2007/075987, WO 2007/075873, and WO 2007/076057, the full disclosures of which are incorporated herein by reference in their entirety for all purposes. The polymerase may comprise a label (e.g., a donor) that undergoes FRET with a label (e.g., an acceptor) attached to one or more of the nucleotide analogs, e.g., where a given analog having a first nucleobase is configured such that the emission spectrum during interaction with the polymerase is detectably distinct from the interaction of any other analog having any other nucleobase. Kits for performing template-directed synthesis reactions may optionally include primer and/or template sequences, as well. Such kits also typically include instructions for use of the compounds and other reagents in accordance with the desired application methods, e.g., nucleic acid sequencing, and the like.

In addition, in particularly preferred aspects, the kits of the invention will typically include a reaction substrate that includes reaction regions for carrying out and observing the analytical reactions, e.g., synthesis reactions for identification of sequence information. Such substrates include, e.g., multi-well micro or nano plates, as well as arrayed substrates, e.g., planar transparent arrays that include discrete reaction regions defined by, e.g., structural, chemical or other means. For example, patterned arrays of complexes may be provided disposed upon planar transparent substrates for observation. Preferably, such substrates provide optical resolvability between individual reactions, e.g., immobilized at different reaction sites on the substrate. Alternatively and preferably, the substrate component comprises an array or arrays of optically confined structures like zero mode waveguides and/or optical waveguide arrays. Examples of arrays of zero mode waveguides are described in, e.g., U.S. Pat. No. 7,170,050, the full disclosure of which is incorporated herein by reference in its entirety for all purposes. Examples of optical waveguide arrays are described, e.g., in U.S. Ser. No. 12/560,308, filed Sep. 15, 2009, and U.S. Patent Publication Nos. 2008/0128627, 2008/0152281, and 2008/01552280.

V. Exemplary Compounds and Methods for Synthesis

Although the exemplary compounds and synthesis schemes provided below are focused on FRET dyes that comprise cyanine dyes, in particular Cy3 and Cy5, the following examples are simply exemplary embodiments of compounds and methods of making such compounds for use in the compositions and methods of the invention. As such, it will be understood that other dyes may also be substituted in these exemplary compounds and synthesis schemes provided.

Figure 4:
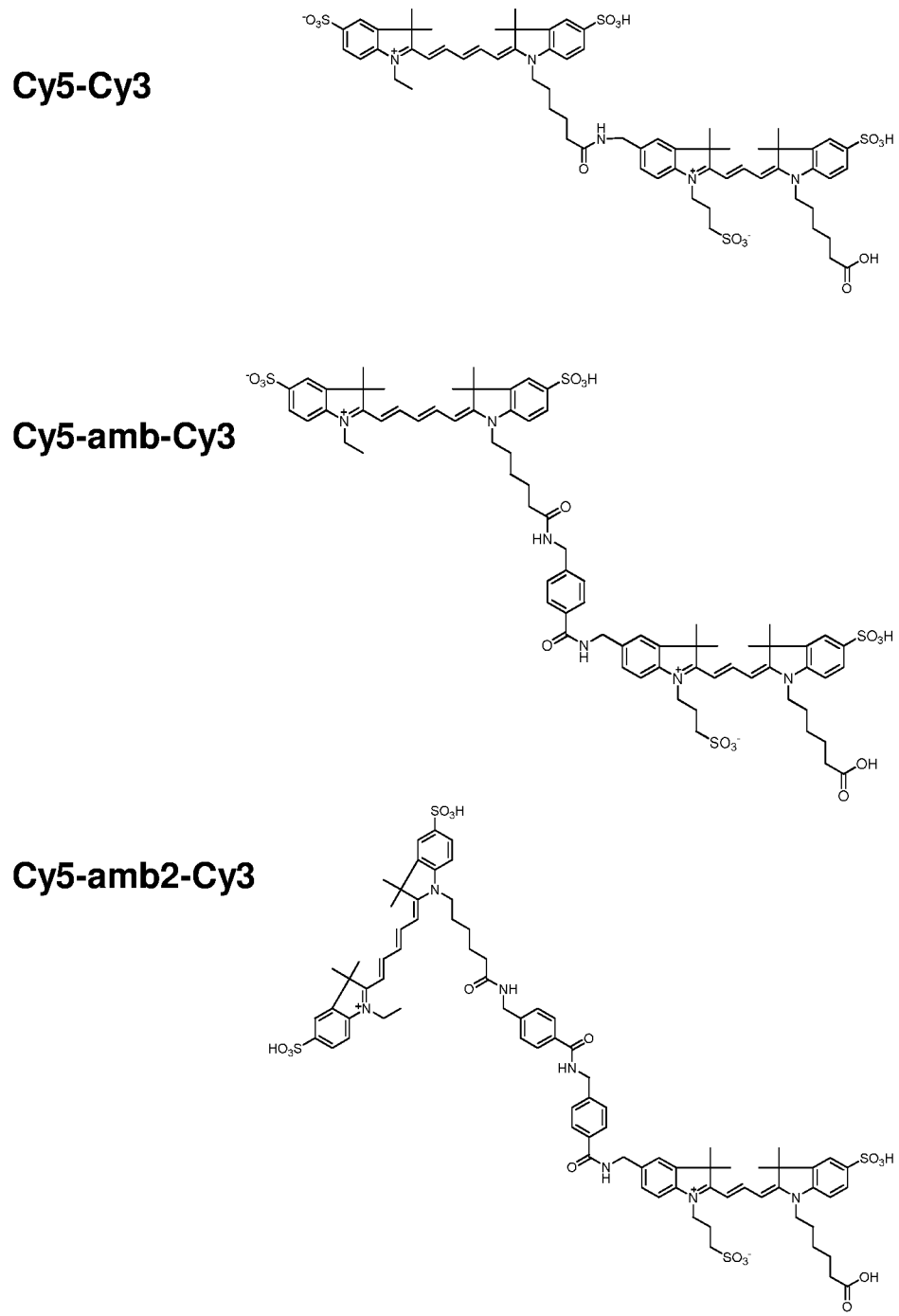
FIG. 4 provides chemical structures for certain embodiments of FRET labels described herein.

FIG. 4 provides structures for three FRET dyes composed of Cy3 and Cy5 fluorescent dye, each of which has an inter-dye linker of a different length. By adding extra aminomethyl benzoic acid (amb) groups between the donor dye (Cy3) and the acceptor dye (Cy5) we can vary the distance between the pair and thus control the energy efficiency as discussed above.

Figure 5:
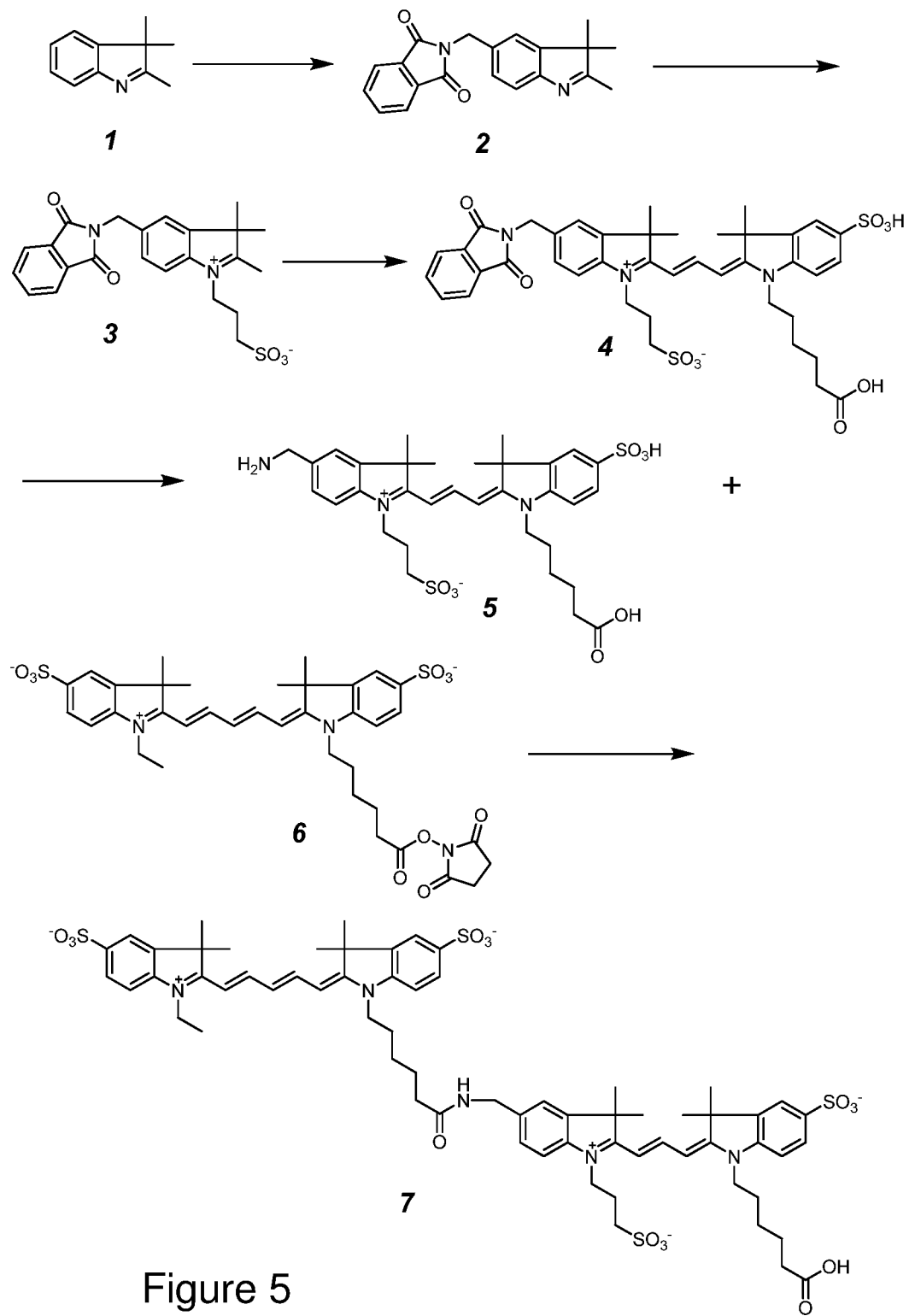
FIG. 5 provides a synthesis scheme for the Cy5-Cy3 compound depicted in FIG. 4.

The compounds of the invention are generally synthesizable using methods known to those of ordinary skill in the art. For example, synthesis of the first structure illustrated in FIG. 4 ("Cy5-Cy3") was carried out and the synthesis scheme is shown in FIG. 5. Specifically, nitration and amidomethylation of 2,3,3-trimethylindolenine (1) with nitric acid and sulfuric acid was followed by reaction with N-(hydroxymethyl)phthalimide gives the phthalimide (2), which was heated with propanesultone to form the quarternary amine (3). Reaction of (3) with N-(5-carboxypentyl)-2,3,3-trimethyl-5-sulfo-indolenine and N,N'-diphenylformamidine gave the carbocyanine compound (4). Deprotection of the phthalimide group with concentrated hydrochloric acid gave the desired bifunctional cyanine dye (5). Coupling of the bifunctional cyanine dye with Cy5-mono NHS ester (6) gave the Cy5-Cy3 FRET dye (7).

Figure 7:
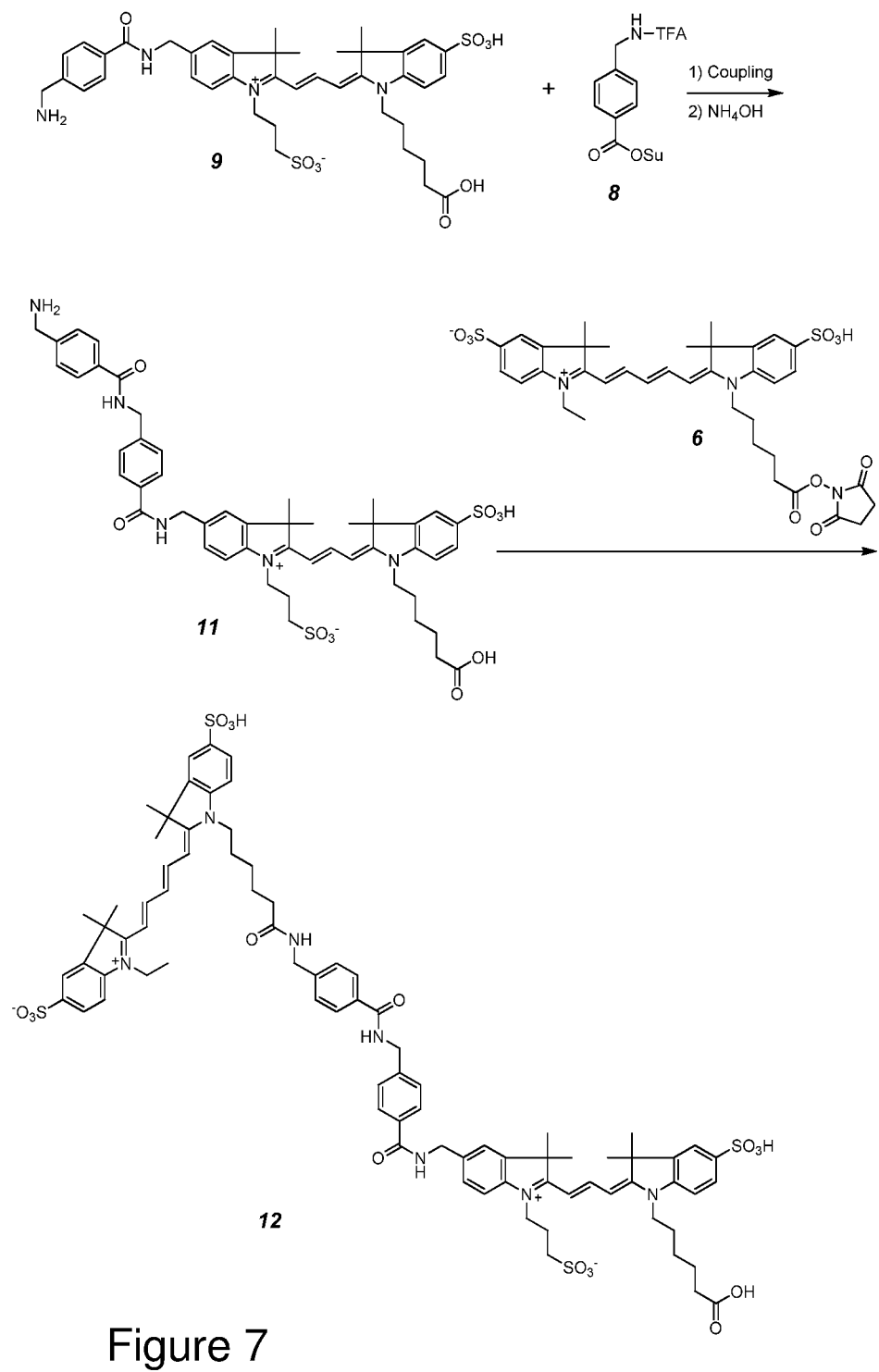
FIG. 7 provides a synthesis scheme for the Cy5-amb2-Cy3 compound depicted in FIG. 4.

Synthesis of the second structure illustrated in FIG. 4 ("Cy5-amb-Cy3") is shown in FIG. 6, and synthesis of the third structure illustrated in FIG. 4 ("Cy5-amb2-Cy3") is shown in FIG. 7. The Cy5-amb-Cy3 label comprises an aminomethyl benzoic acid linking the two dye molecules; and the Cy5-amb2-Cy3 label comprises two aminomethyl benzoic acid groups linking the two dye molecules. Reaction of the amino carboxylic acid bifunctional cyanine compound (5) with the trifluoroacetate (TFA) protected aminomethylbenzoic NHS ester (8) in N,N-dimethylformamide followed by hydrolysis with ammonium hydroxide gives the Cy3-amb-NH2 (9). Coupling of Cy3-amb-NH2 (9) with Cy5-mono NHS ester (6) gives the Cy5-amb-Cy3-FRET dye (10). Similarly, the Cy5-amb2-Cy3 FRET dye (12) can then be prepared starting with Cy3-amb-NH2 (9) following the same steps as described above.

Figure 8:
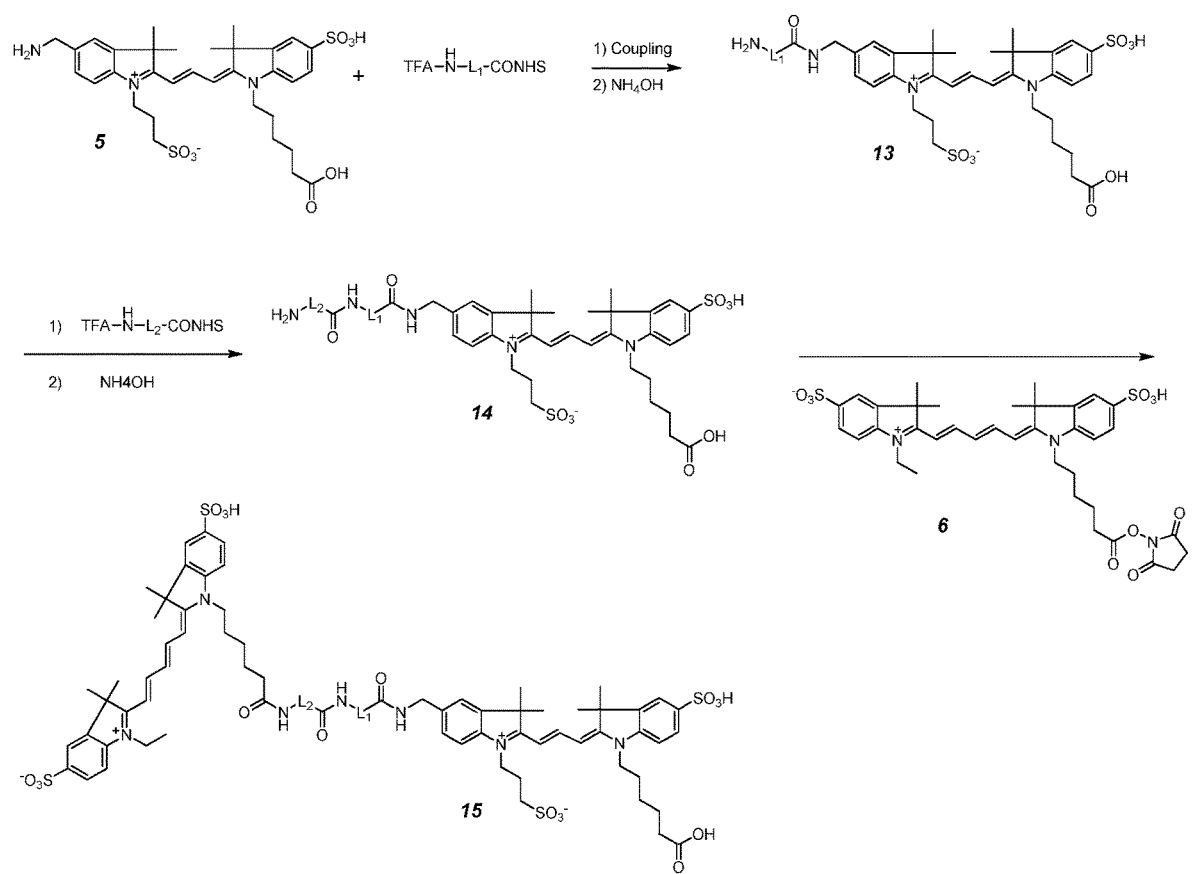
FIG. 8 provides a general synthesis scheme for Cy5-Cy3 compounds.

FIG. 8 provides a general synthetic strategy for the preparation of Cy5-Linker-Cy3 FRET dyes following the same synthetic approaches as described above for the preparation of Cy5-amb2-Cy3 (12). Reaction of the amino carboxylic acid bifunctional cyanine compound (5) with a TFA protected linker-1 NHS ester followed by hydrolysis with ammonium hydroxide gives the Cy3-L1-NH2 (13). Coupling of the Cy3-L1-NH2 (13) with a second TFA protected linker-2 NHS ester and again followed by hydrolysis with ammonium hydroxide gives the double linker cyanine dye, Cy3-L1-L2-NH2 (14), which then reacts with Cy5-mono-NHS ester to give the desired Cy5-L2-L1-Cy3 FRET dye (15). The same procedure can also be applied for the synthesis of a Cy5-multiple linkers-Cy3 FRET dyes.

Figure 9:
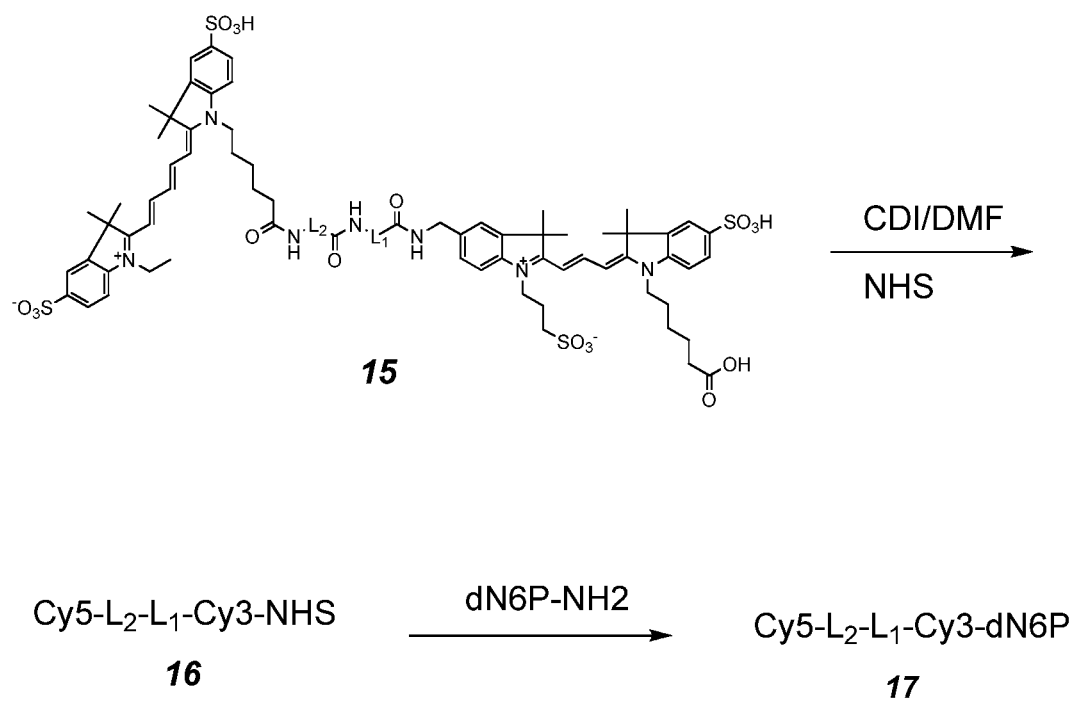
FIG. 9 illustrates a synthesis scheme for constructing nucleotide analogs bearing FRET labels.

FIG. 9 illustrates one embodiment of a synthetic scheme for construction of FRET-labeled nucleotide analogs comprising a hexaphosphate chain. Transformation of the Cy5-linkers-Cy3-COOH (15) to the corresponding NHS ester can be achieved with various activation methods, such as the classical CDI/NHS, TSTU, EDAC/NHS or DCC/NHS. The resultant NHS ester (16) is then coupled to the aminohexaphosphate deoxy nucleotide to give the corresponding FRET-labeled nucleotide analog (17).

Figure 10:
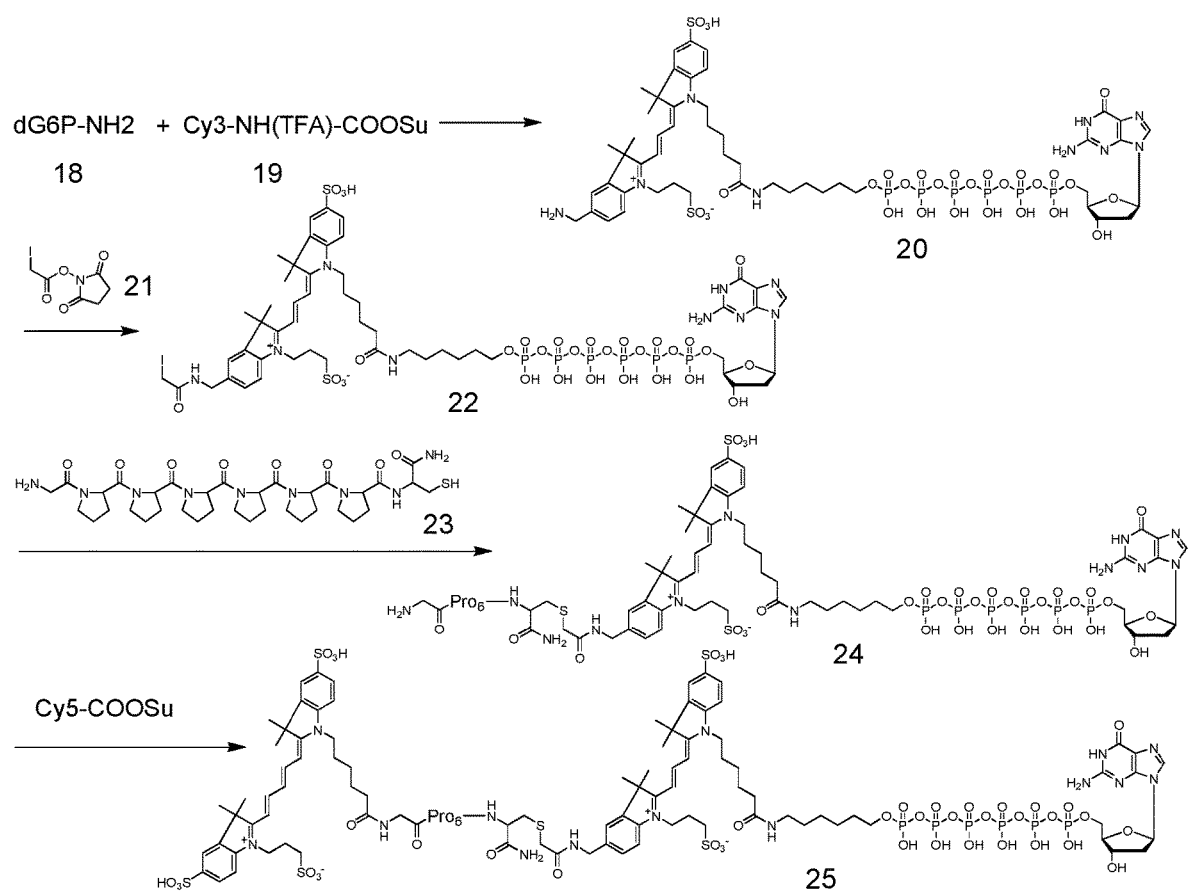
FIG. 10 provides a synthesis scheme for Cy5-pro6-Cy3-dG6P.

FIG. 10 depicts an example of using polyproproline as the rigid linker, and the synthesis of Cy5-pro6-Cy3-dG6P is demonstrated. Reaction of aminohexaphosphate deoxyguanosine, dG6P-NH2 (18), with TFA protected Cy3 NHS ester (19) followed by hydrolysis with ammonium hydroxide gives the compound dG6P-Cy3-NH2 (20). Reaction of dG6P-Cy3-NH2 (20) with iodoacetic acid N-hydroxysuccinimide ester (21) gives the corresponding adduct, compound (22), which then reacts with the amino hexaproline thiol (23) to give the coupling product (24). Reaction of compound (24) with Cy5-mono NHS ester gives the FRET-labeled nucleotide analog (25) which has a rigid hexaproline linker between the donor Cy3 dye and the acceptor Cy5 dye.

Figure 11:
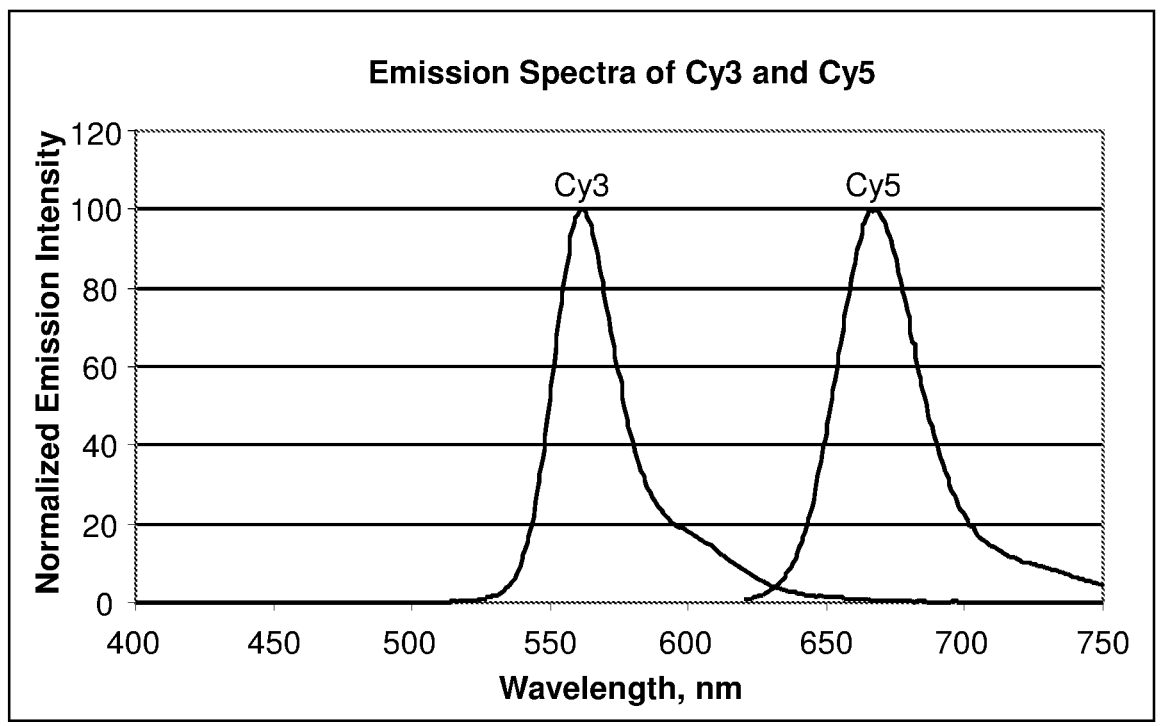
FIG. 11 illustrates individual emission spectra for Cy3 and Cy5.
Figure 12:
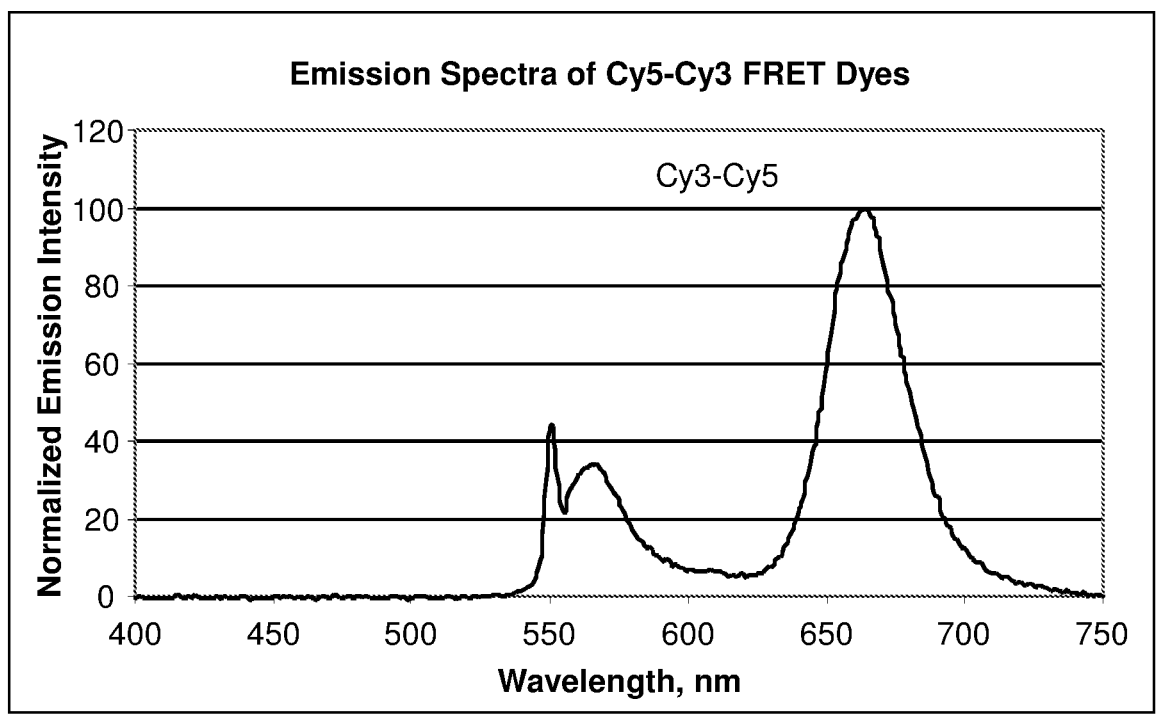
FIG. 12 illustrates an individual emission spectrum for a Cy5-Cy3 FRET dye.
Figure 13:
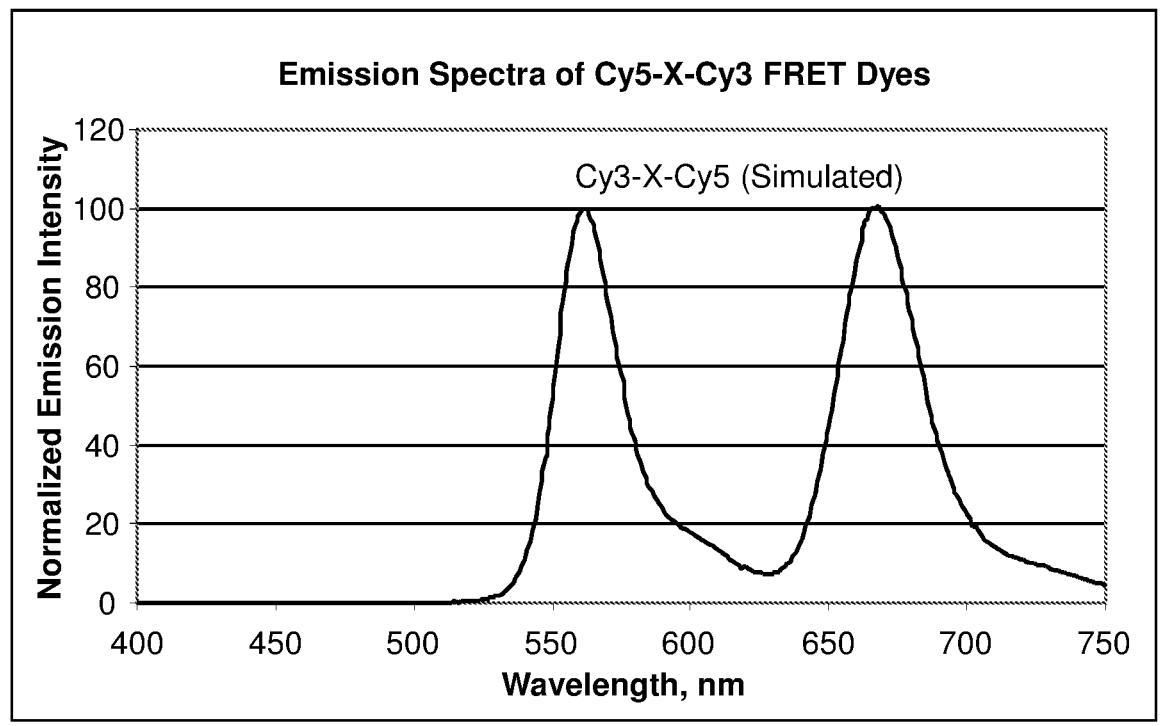
FIG. 13 illustrates an individual emission spectrum for a Cy5-X-Cy3 FRET dye.
Figure 14:
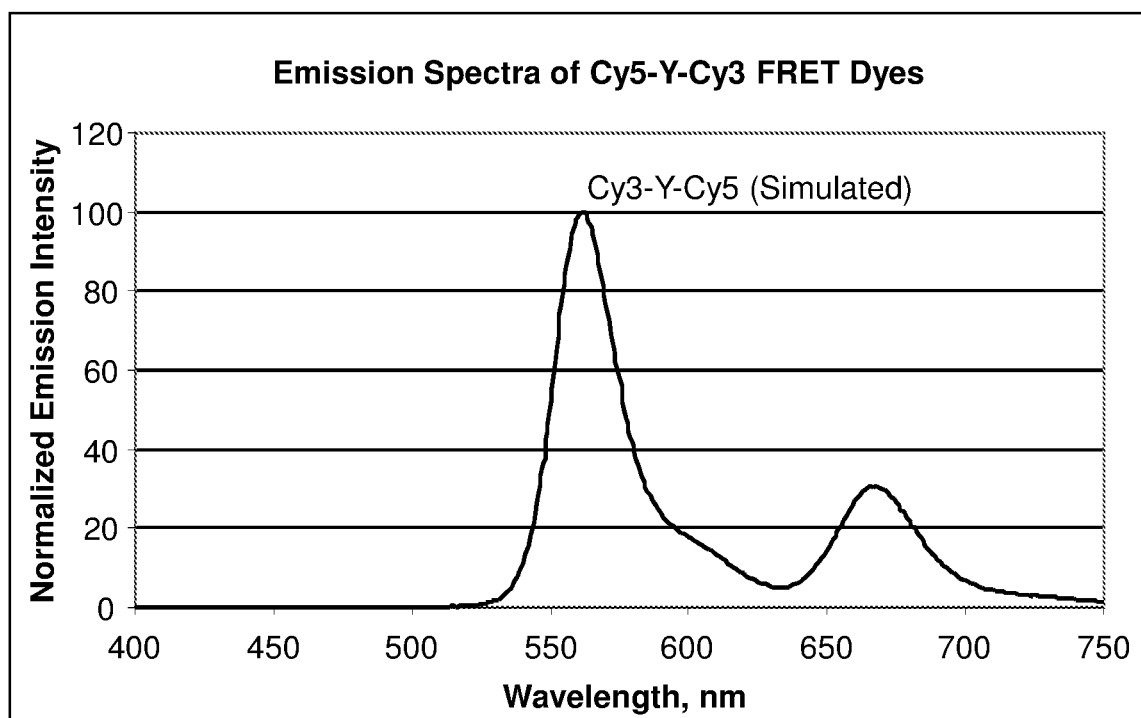
FIG. 14 illustrates an individual emission spectrum for a Cy5-Y-Cy3 FRET dye.

FIG. 11 provides emission spectra for Cy5 and Cy3 dyes. FIG. 12 provides an emission spectrum for a Cy5-Cy3 FRET dye exhibiting an energy transfer of greater than 50%. The FRET transfer from Cy3 to Cy5 changes the ratio of the intensities of Cy3 to Cy5 emissions such that the intensity of the Cy3 emission is approximately one-fourth that of the Cy5 emission. FIG. 13 depicts a computer-simulated emission spectrum of a compound Cy5-X-Cy3 that shows a 50% energy transfer that provides for a ratio of intensities of Cy3 to Cy5 emissions that is approximately 1:1. FIG. 14 depicts a computer-simulated emission spectra of a compound Cy5-Y-Cy3 that shows a less than 50% energy transfer, which changes the ratio of the intensities of Cy3 to Cy5 emissions such that the intensity of the Cy3 emission is approximately four-fold greater that of the Cy5 emission. As described herein, these unique fluorescent emission spectra can be used as markers for different labeled compounds in analytical reactions. For example, in some preferred embodiments, such labeled compounds are labeled nucleotides in sequencing-by-synthesis analytical reactions using only one laser source to provide emission spectra that identify the nucleobase in a given labeled nucleotide incorporated into a nascent nucleic acid strand.

Although described in some detail for purposes of illustration, it will be readily appreciated that a number of variations known or appreciated by those of skill in the art may be practiced within the scope of present invention. For example, although some of the exemplary FRET labels and labeled compounds described in the specification and figures comprise Cy3 and Cy5 fluorescent dyes, the compounds, compositions, and methods are not limited to the cyanine dyes and other groups of fluorescent dyes such as rhodamine derivatives (e.g., Alexa dyes (Molecular Probes/Invitrogen/Life Technologies) and Dylight dyes (Dyomics/Thermo Fisher Scientific)), and other labeling moieties known in the art (e.g., quantum dots) can be selected as candidates for either the donor dyes or the acceptor dyes. While various embodiments herein are discussed in terms of their application to single molecule sequencing, e.g., using ZMWs, it will be appreciated that the methods and systems are also applicable for use with monitoring of other enzymatic systems, e.g., immunoassays, drug screening, and the like, and/or in non-confined detection systems, e.g., systems that do not use ZMWs or similar confinement schemes. Further, although some of the embodiments are described in terms of specific types of reaction components (e.g., nucleotide analogs, tRNA analogs, and the like), the invention is not limited to use with these exemplary reaction components and the various types of intramolecular and intermolecular FRET labels provided herein can be used on countless other types of reaction components known to those of ordinary skill in the art. All terms used herein are intended to have their ordinary meaning unless an alternative definition is expressly provided or is clear from the context used therein. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entireties for all purposes.

What is claimed is:

1. A kit for performing a sequencing-by-synthesis reaction, comprising:
    first and second nucleotide analogs, wherein the first nucleotide analog comprises a first fluorescent label that produces a first signal in response to excitation illumination, and the second nucleotide analog comprises a second fluorescent label that produces a second signal in response to excitation illumination, wherein the first and second signals have distinct signal intensities, and wherein the first and second signals comprise peaks at the same wavelengths wherein during incorporation of the first or second nucleotide analogs the first or second fluorescent labels are removed, and
    a polymerase enzyme for performing template-dependent synthesis employing the labeled nucleotide analogs.

2. The kit of claim 1, wherein at least one of the first and second signals comprises distinct emission signal intensities at a plurality of different wavelengths.

3. The kit of claim 1, wherein the first fluorescent label comprises a first FRET label having a first FRET efficiency, and the second fluorescent label comprises a second FRET label having a second FRET efficiency different from the first FRET efficiency, wherein the first FRET label and the second FRET label each comprise at least two chromophores that engage in FRET.

4. The kit of claim 1, wherein the first and second FRET efficiencies are from about 0 to about 100% of a maximum FRET efficiency for each of the first and second FRET labels.

5. The kit of claim 1, wherein the kit further comprises at least a third nucleotide analog, the third nucleotide analog comprising a third fluorescent label producing a third signal in response to excitation illumination, the third signal differing from each of the first and second signals by at least one of its emission intensity and its emission spectrum.

6. The kit of claim 1, wherein the kit further comprises at least a fourth nucleotide analog, the fourth reactant comprising a fourth fluorescent label producing a fourth signal in response to excitation illumination, the fourth signal differing from each of the first, second and third signals by at least one of its emission intensity and its emission spectrum.

7. The kit of claim 1, wherein the kit further comprises at least four different nucleotide analogs, namely those that are analogous to A, T, G, and C, where each bears a detectably different labeling group to permit its individual identification in the presence of the others.

8. The kit of claim 1, wherein the kit further comprises two additional nucleotide analogs, wherein at least one of the first, second, and additional nucleotide analogs comprises a FRET label and one other comprises a non-FRET label.

9. The kit of claim 1, wherein the first and second nucleotide analogs comprise FRET labels having the same constituent FRET label moieties in different orientations.

10. The kit of claim 1, wherein the kit further comprises nucleotide analogs having multiple labeling moieties that do not undergo FRET.

11. The kit of claim 1, wherein the polymerase is a phi29 polymerases.

12. The kit of claim 1, wherein the kit further comprises a sequencing primer.

13. The kit of claim 1, wherein the kit further comprises one or more solutions for performing a sequencing reaction.

14. The kit of claim 1, wherein the kit further comprises dye standards for detector calibration.

* * * * *